United States Patent
Hansen et al.

(10) Patent No.: US 12,263,037 B2
(45) Date of Patent: Apr. 1, 2025

(54) ULTRASOUND-BASED INTRAVASCULAR PLACEMENT GUIDE STRUCTURE

(71) Applicant: Oregon Health & Science University, Portland, OR (US)

(72) Inventors: Matthew Hansen, Portland, OR (US); Amen Mengistu, Portland, OR (US); Adam Hoiness, Austin, TX (US); Lauren Larocco, Sacramento, CA (US)

(73) Assignee: Oregon Health & Science University, Portland, OR (US)

( * ) Notice: Subject to any disclaimer, the term of this patent is extended or adjusted under 35 U.S.C. 154(b) by 207 days.

(21) Appl. No.: 17/999,526

(22) PCT Filed: May 6, 2021

(86) PCT No.: PCT/US2021/031188
§ 371 (c)(1),
(2) Date: Nov. 21, 2022

(87) PCT Pub. No.: WO2021/236348
PCT Pub. Date: Nov. 25, 2021

(65) Prior Publication Data
US 2023/0200777 A1    Jun. 29, 2023

Related U.S. Application Data

(60) Provisional application No. 63/028,362, filed on May 21, 2020.

(51) Int. Cl.
  A61B 8/00    (2006.01)
  A61B 8/08    (2006.01)

(52) U.S. Cl.
  CPC .......... *A61B 8/4227* (2013.01); *A61B 8/0891* (2013.01)

(58) Field of Classification Search
  CPC .. A61B 8/4227; A61B 8/4209; G10K 11/004; G10K 11/352
  See application file for complete search history.

(56) References Cited

U.S. PATENT DOCUMENTS 4,304,133 A * 12/1981 Feamster, III ....... G10K 11/352
                                                        73/633
4,442,844 A *  4/1984 Navach ................ A61B 8/4227
                                                        600/407

(Continued)

*Primary Examiner* — Serkan Akar
*Assistant Examiner* — Aminah Asghar
(74) *Attorney, Agent, or Firm* — Foster Garvey P.C.

(57) ABSTRACT

A guide structure (10) is configured for placement on a patient's skin and holding a medical probe (61) for adjustable positioning over the patient's skin during vascular line placement. A preferred guide structure includes a U-shaped base (12) having two arms (14, 16) separated by an open space (18). A carriage (50) for a medical probe holder (60) is movable along carriage guide surfaces (40, 42) of the arms of the base and thereby forms a movable bridge spanning the open space. The medical probe holder carrying a medical probe is movable in a direction transverse to the arms of the base to set the medical probe to a desired distance into the open space. A carriage translation actuator (62) operatively associated with the carriage enables movement of the carriage and thereby adjusts the position of the medical probe over the surface of the patient's skin.

21 Claims, 23 Drawing Sheets

(56) References Cited

U.S. PATENT DOCUMENTS

| | | | | |
|---|---|---|---|---|
| 5,254,123 | A * | 10/1993 | Bushey | A61B 17/3403 606/130 |
| 6,261,231 | B1 * | 7/2001 | Damphousse | G10K 11/004 600/459 |
| 9,649,075 | B2 | 5/2017 | Defreitas et al. | |
| 2003/0104339 | A1 * | 6/2003 | Fromovich | A61C 8/0033 606/105 |
| 2003/0167004 | A1 * | 9/2003 | Dines | A61B 8/0825 600/437 |
| 2005/0215878 | A1 * | 9/2005 | Zan | A61B 8/4461 600/407 |
| 2010/0174185 | A1 | 7/2010 | Wang et al. | |
| 2011/0282212 | A1 | 11/2011 | Hyoun et al. | |
| 2012/0143083 | A1 * | 6/2012 | Kwai | A61B 90/17 600/567 |
| 2016/0242707 | A1 * | 8/2016 | DeFreitas | A61B 6/0414 |
| 2018/0177487 | A1 * | 6/2018 | Deffieux | A61B 8/0816 |
| 2019/0021695 | A1 * | 1/2019 | Watts | A61B 8/0891 |
| 2019/0099154 | A1 * | 4/2019 | Adachi | A61B 8/5253 |

* cited by examiner

ULTRASOUND-BASED INTRAVASCULAR PLACEMENT GUIDE STRUCTURE

RELATED APPLICATIONS

The present application is a National Stage of International Application No. PCT/US2021/031188, filed May 6, 2021, which claims priority to U.S. Provisional Application No. 63/028,362, filed on May 21, 2020, which are hereby incorporated by reference in their entireties.

COPYRIGHT NOTICE

© 2022 Oregon Health & Science University. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

Generally, the field relates to placement of intravascular lines. More specifically, the field involves ultrasound-guided placement of vascular lines in the blood vessels of the extremities. The ultrasound-guided intravascular placement device is engineered to offer mechanical assistance to sonographers performing an ultrasound-guided intravenous or intra-arterial vascular access procedure.

BACKGROUND INFORMATION

Intravenous line (IV) placement is a procedure performed in most medical contexts and is the most prevalent procedure performed in the emergency department (ED), with 150-200 million IVs placed annually in North America. (Fields J M, Plela N E, AuAK, et al. Risk factors associated with difficult venous access in adult ED patients. *Am J Emerg Med.* 2014; 32(1):1179-82; Alexandrou E. The One Million Global Catheters PIVC worldwide prevalence study. *Br J Nurs.* 2014; 23(8):S16-7. ) However, patients who are obese, are diabetic, or have a history of drug use or sickle cell disease are associated with difficult IV placements. Frequently, these patients require alternative intravenous line placement such as external jugular line or central venous catheter (CVC) insertion, which are associated with serious complications when compared to IVs. (McGee D C, Gould M K. Preventing complications of central venous catheterization. *N Engl J Med.* 2003; 348(12):1123-33; Trick W E, Miranda J, Evans A T, et al. Prospective cohort study of central venous catheters among internal medicine ward patients. *Am J Infect Control.* 2006; 34(10):636-41. ) Moreover, placement of such alternative intravenous line placements may have to be performed by medical practitioners having a specialized scope of practice, increasing cost. Use of ultrasound in real-time for IV insertion can improve placement success in patients with difficult intravenous access. (Keyes L E, Frazee B W, Snoey E R, et al. Ultrasound-guided brachial and basilica vein cannulation in emergence department patients with difficult intravenous access. *Ann Emerg Med.* 1999; 34(6):711-4; Costantino T G, Parkh A K, Satz W A, et al. Ultrasonography-guided peripheral intravenous access versus traditional approaches in patients with difficult intravenous access. *Ann Emerg Med.* 2005; 46(5):456-61. )

However, ultrasound-guided IV placement can be difficult to perform for many sonographers, requiring a significant training burden to obtain competency. For example, in the most common approach, short-axis placement (e.g., transverse or out-of-plane visualization), the sonographer alternates between visualizing the vein and needle tip until the need tip enters the vein, requiring that the ultrasound transducer be advanced in synchronism with the needle tip, as both the needle tip and needle shaft may appear similar. (Gottlieb M, Sundaram T, Holladay D, et al. Ultrasound-guided peripheral intravenous line placement: a narrative review of evidence-based best practices. *WestJEM.* 2017; 18(6):1047-54.)

While the short-axis approach often is utilized by more novice sonographers (due to a relatively reduced training burden), it has been associated with increased risk of injury to posterior vessel walls. (Blaivas M, Brannam L, Fernandez E. Short-axis versus long-axis approaches for teaching ultrasound-guided vascular access on a new inanimate model. *Acad Emerg Med.* 2003; 10(12):1307-11; Mahler S A, Wang H, Lester C, et al. Short- vs long-axis approach. *Am J Emerg Med.* 2010; 28(3):343-7. ) In contrast, long-axis placement (e.g., in-plane visualization) allows better needle tip visualization and less risk of posterior vessel wall injury. (Blaivas et al 2003; Mahler et al. 2010. ) However, the long-axis approach still requires that the sonographer visualize the needle and vessel in the same plane when advancing the needle tip. In this orientation, slight movements in the probe can move the needle out of plane, creating a significant challenge for some sonographers. (Gottlieb et al., 2017. )

In addition, arterial access is often obtained via the radial artery, or other arteries of the extremities, for invasive real-time monitoring of the blood pressure, or for cardiac or other arterial angiographic procedures.

SUMMARY OF THE DISCLOSURE

A guide structure is configured for placement on a patient's skin and holding a medical probe to adjustably position it over a region of the patient's skin during vascular line placement. Some of the disclosed embodiments are configured to hold an ultrasonic medical probe. A preferred guide structure includes a base configured to rest on a surface of a patient's skin. The base includes first and second arms separated by an open space and respective first and second open ends and respective first and second closed ends that are interconnected by a medial section. The first arm has a first interior surface and a first exterior surface, and the second arm has a second interior surface and a second exterior surface, with the first and second interior surfaces being opposed to each other.

A first carriage guide surface preferably extends lengthwise between the first open and closed ends of the first arm. A second carriage guide surface preferably extends lengthwise between the second open and closed ends of the second arm, with the first and second carriage guide surfaces being plane parallel to each other.

A preferred guide structure has a carriage including an undercarriage and a carriage post. The undercarriage includes first and second support portions that laterally extend in opposite directions, with the first and second support portions configured to move along the respective first and second carriage guide surfaces and thereby form a movable bridge spanning the open space separating the first and second arms of the base. A medical probe holder is preferably operatively connected to the carriage post and configured for motion transverse to the first and second arms to set, to a desired distance into the open space separating the first and second arms, a medical probe placed in the device holder.

A preferred guide structure has a carriage translation actuator in operative association with the undercarriage to move the carriage and thereby adjust the position of the medical probe over the surface of a patient's skin on which the base has been set.

In some embodiments, the guide structure includes first and second spaced-apart shaft tunnels that extend in a direction transverse to the first and second arms of the base. In other embodiments, the guide structure further comprises first and second carriage adjustment channels. The first carriage adjustment channel is formed lengthwise between the first open and closed ends of the first arm and includes a lengthwise extending first gear rack, and the second carriage adjustment channel is formed lengthwise between the second open and closed ends of the second arm and includes a lengthwise extending second gear rack. The first and second carriage adjustment channels are spatially aligned with each other and are in spaced apart relation to the first and second carriage guide surfaces. An actuator shaft is sized to fit into one of the first and second channels and has opposite ends on which first and second drive gears are set to mesh with the respective first and second gear racks. A follower shaft is sized to fit into the other one of the first and second shaft tunnels and has opposite ends on which first and second follower gears are set to mesh with the respective first and second drive gears. The operative association of the carriage translation actuator and the carriage includes, in response to a rotational force applied to the actuator shaft, rotation of the actuator shaft and thereby rotation of the follower shaft and movement of the carriage to adjust the position of the medical probe over the surface of a patient's skin on which the base has been set.

In further embodiments, the guide structure further comprises first and second bracing spurs that are positioned on, respectively, the first and second arms of the base of the guide structure for impeding a patient's skin from entering the open space of the base. In a first alternative embodiment, the first and second bracing spurs are positioned on, respectively, the first and second open ends of the first and second arms of the base. In a second alternative embodiment, the first and second bracing spurs are positioned on, respectively, the first and second interior surfaces of the first and second arms of the base. In a third alternative embodiment, the first and second bracing spurs have curved skin-facing aspects for contouring the first and second bracing spurs to the surface of a patient's skin.

In other embodiments, the guide structure further comprises first and second restraint anchors that are positioned on, respectively, the first and second exterior surfaces of the base of the guide structure for supporting a limb restraint, neck restraint, or torso restraint configured to secure the guide structure to a patient's skin.

In further embodiments, the first and second restraint anchors are, respectively, positioned proximal to the first and second closed ends of the base of the guide structure relative to its first the second open ends to facilitate compression of the patient's skin at a location the is proximal relative to a needle insertion site.

Additional aspects and advantages will be apparent from the following detailed description of preferred embodiments, which proceeds with reference to the accompanying drawings.

DETAILED DESCRIPTION OF PREFERRED EMBODIMENTS

Figure 1A:
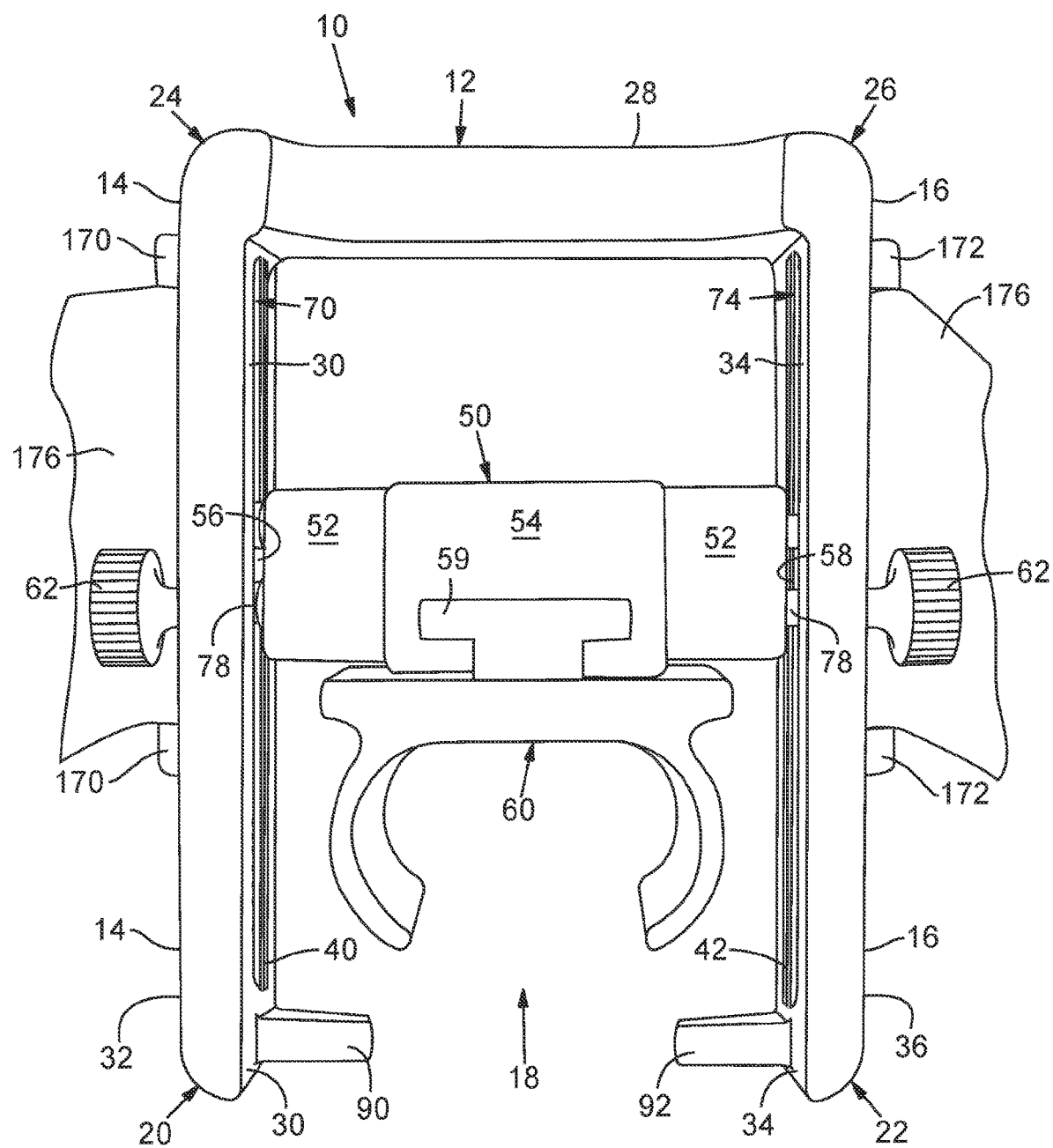
FIG. 1A is a top plan view showing a guide structure that includes first and second arms of a base interconnected by a medial section and a carriage forming a movable bridge spanning an open space.
Figure 1B:
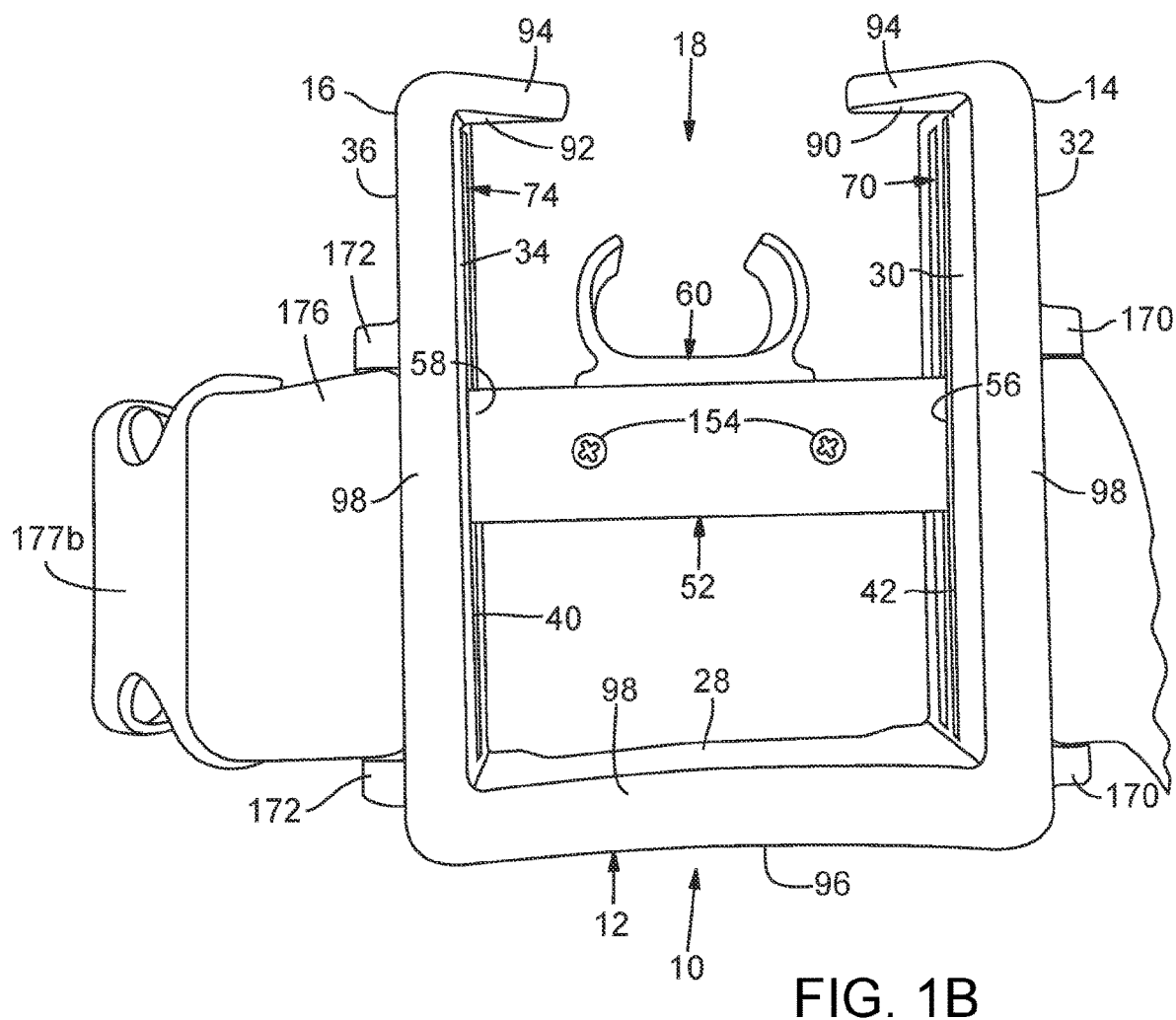
FIG. 1B is a bottom plan view of skin-facing aspects of the guide structure of FIG. 1A and an undercarriage of the movable bridge.

FIG. 1A is a top plan view showing an embodiment of an ultrasound-guided intravenous placement guide structure 10 having a base 12 configured to rest on a patient's skin. FIG. 1B is a bottom plan view showing the skin-facing aspects of base 12 of guide structure 10. In the embodiment shown, base 12 includes a first arm 14 and a second arm 16 separated by an open space 18. First arm 14 and second arm 16 have, respectively, a first open end 20 and a second open end 22 and have, respectively, a first closed end 24 and a second closed end 26 interconnected by a medial section 28. First arm 14 has a first interior surface 30 and a first exterior surface 32, and second arm 16 has a second interior surface 34 and a second exterior surface 36, with first interior surface 30 and second interior surface 34 being opposed to each other. A first carriage guide surface 40 is formed on first interior surface 30, and a second carriage guide surface 42 is formed on second interior surface 34. First carriage guide surface 40 extends between first open end 20 and first closed end 24 of first arm 14, and second carriage guide surface 42 extends between second open end 22 and second closed end 26 of second arm 16. In the embodiment shown, first carriage guide surface 40 and second carriage guide surface 42 are plane parallel to and spatially aligned with each other to facilitate guided movement of a carriage 50. Carriage 50 includes an undercarriage 52 and a carriage post 54. Undercarriage 52 has a first support portion 56 and second support portion 58 that extend laterally in opposite directions and are configured to move along respective first carriage guide surface 40 and second carriage guide surface 42 to thereby form a movable bridge spanning open space 18 separating first arm 14 and second arm 16. Carriage post 54 has a notch 59 that is configured to receive a medical probe holder 60 for sliding motion transverse to first arm 14 and second arm 16 of base 12. The sliding motion facilitates setting, to a desired distance into open space 18 separating first arm 14 and second arm 16, a medical probe 61 (FIGS. 5, 6, and 8) placed in medical probe holder 60. Tightening a flat-tipped pressure screw 61s passing through carriage post 54 secures in place medical probe holder 60 and thus medical probe 61 at the desired distance.

Figure 2A:
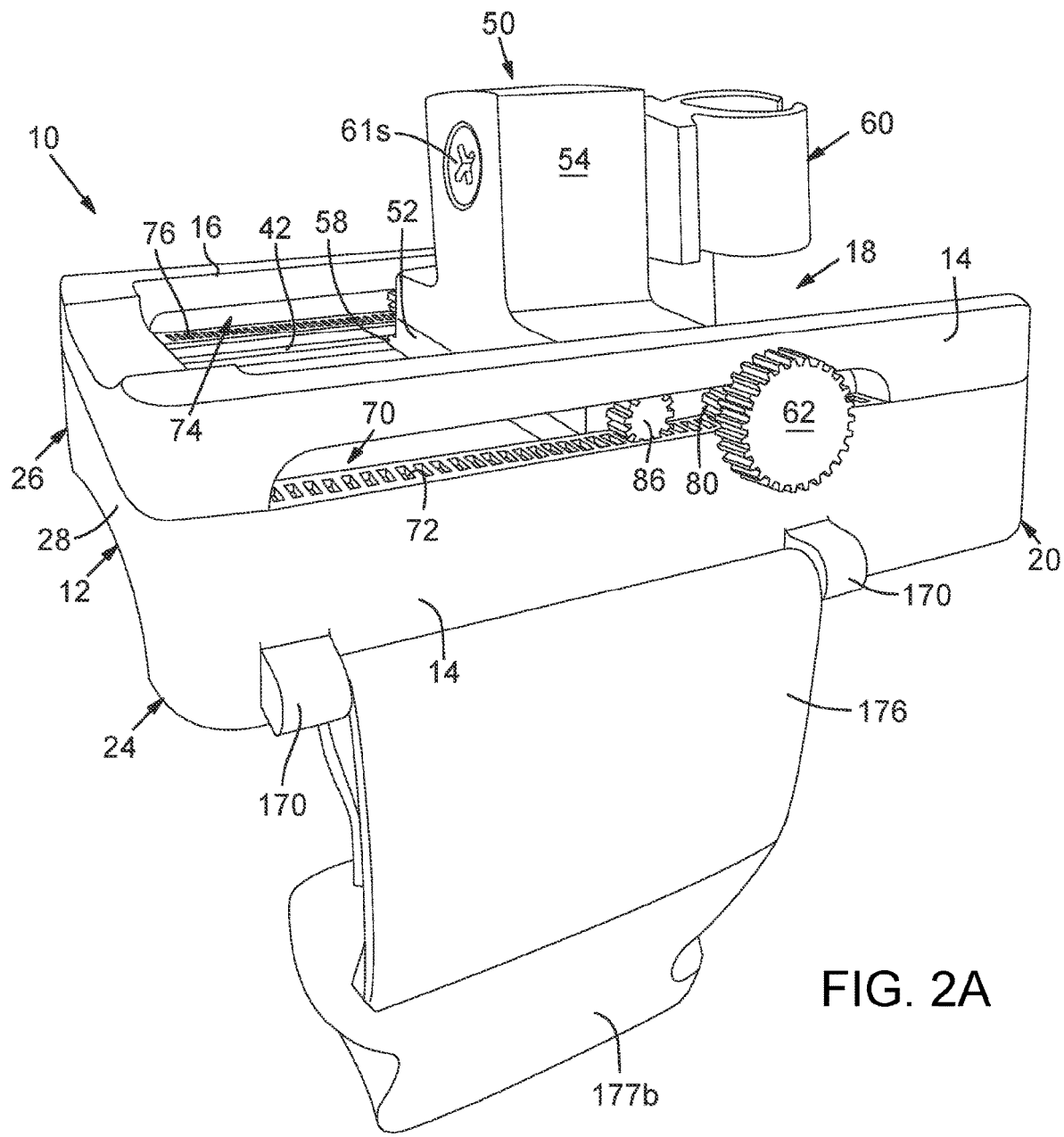
FIGS. 2A and 2B are respective oblique left- and right-side views of a preferred embodiment of the disclosed guide structure showing a carriage translation actuator in operative association with the carriage to move the undercarriage along respective first and second carriage guide surfaces.
Figure 2B:
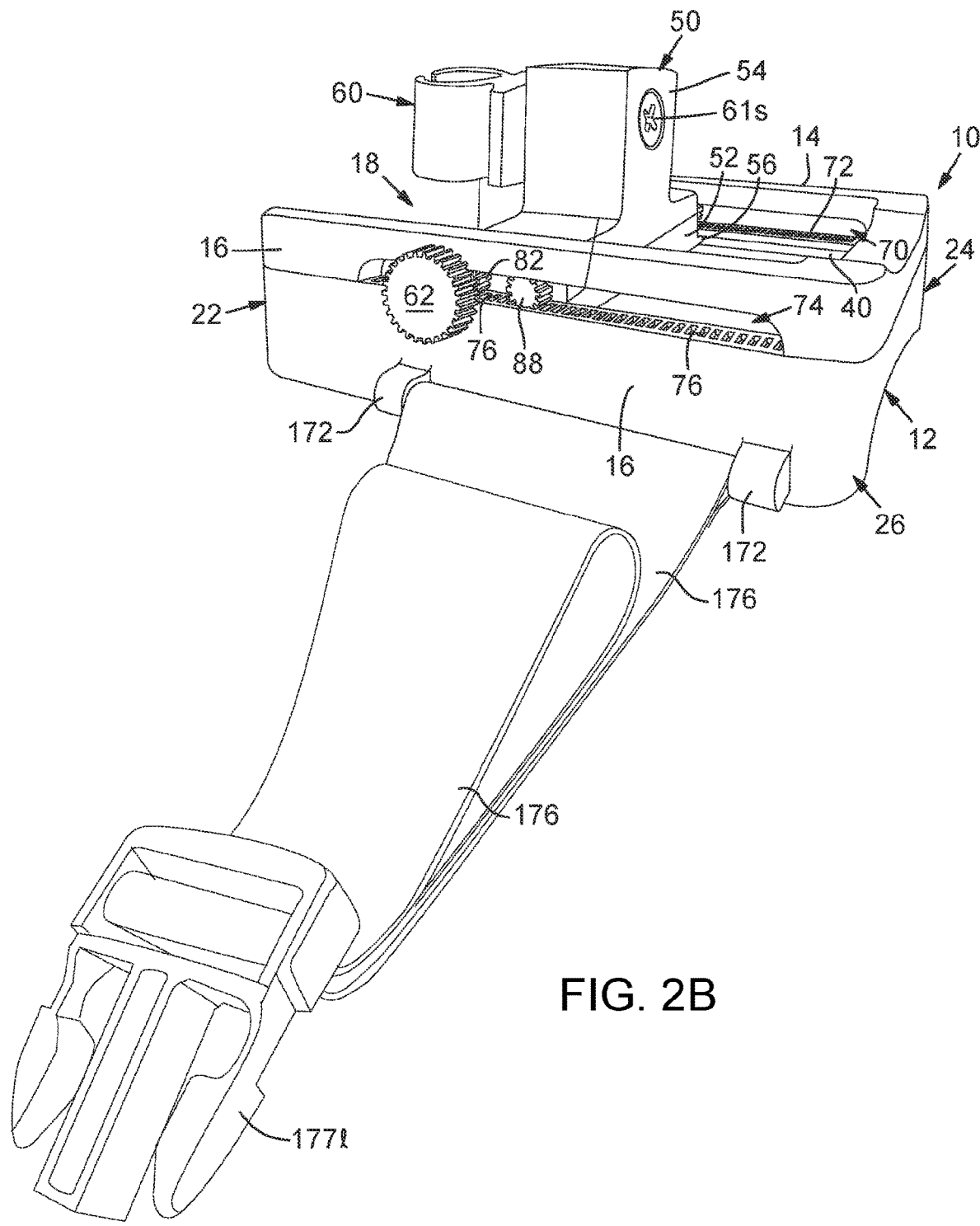

FIGS. 2A and 2B are respective oblique back-left and back-right side views showing guide structure 10 having carriage post 54 operatively connected to medical probe holder 60 that is configured for motion transverse to first arm 14 and second arm 16 to set, to a desired distance into open space 18 separating first arm 14 and second arm 16 of base 12, medical probe 61 placed in medical probe holder 60. In the embodiment shown and as described below, a carriage translation actuator 62 is operatively associated with undercarriage 52 to move carriage 50 along first carriage guide surface 40 and second carriage guide surface 42 and thereby adjust the position of the medical probe placed in medical probe holder 60 over the surface of a patient's skin on which base 12 has been set and secured in place. In some embodiments, carriage 50 includes a first shaft tunnel 64 and a second shaft tunnel 66 that are spaced apart from each other. Shaft tunnels 64 and 66 extend in directions transverse to first arm 14 and second arm 16, as shown in FIGS. 2A and 2B.

A first carriage adjustment channel 70 is formed lengthwise between first open end 20 and first closed end 24 and includes a lengthwise extending first gear rack 72, as shown in FIG. 2A; and a second carriage adjustment channel 74 is formed lengthwise between second open end 22 and second closed end 26 and includes a lengthwise extending second gear rack 76, as shown in FIG. 2B. First carriage adjustment channel 70 and second carriage adjustment channel 74 are spatially aligned with each other and are in spaced-apart relation to first carriage guide surface 40 and second carriage guide surface 42.

Figure 3A:
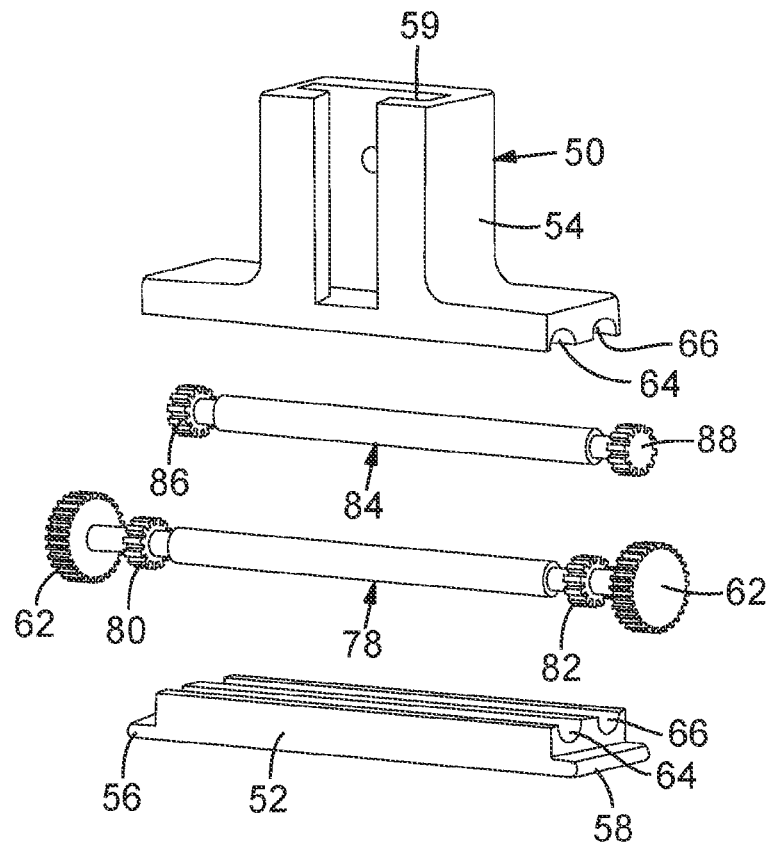
FIG. 3A is an exploded view showing an actuator shaft and a follower shaft sized to fit into first and second shaft tunnels of a carriage.
Figure 3B:
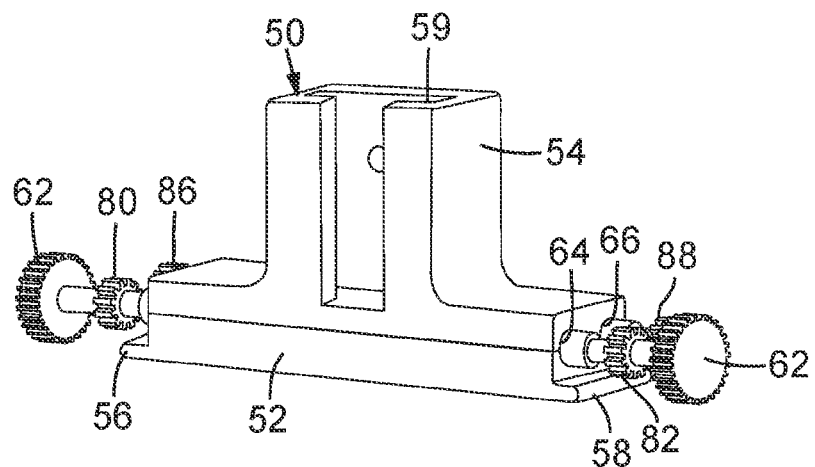
FIG. 3B is an oblique view of the actuator shaft and follower shaft assembled in the carriage shown in FIG. 3A.

FIGS. 3A and 3B are respective oblique exploded and oblique assembly views showing a preferred embodiment of carriage translation actuator 62 that includes an actuator shaft 78 sized to fit into first shaft tunnel 64 of carriage 50 (shown as an assembly in FIG. 3B) and has opposite ends on which a first drive gear 80 and a second drive gear 82 are set to mesh, respectively, with the first gear rack 72 and second gear rack 76, as shown in FIGS. 2A and 2B. A follower shaft 84 is sized to fit into second shaft tunnel 66 of carriage 50 (as shown as an assembly in FIG. 3B) and has opposite ends on which a first follower gear 86 and second follower gear 88 are set to mesh, respectively, with first gear rack 72 and second gear rack 76, as shown in FIGS. 2A and 2B. Skilled persons will appreciate that the positions of actuator shafts 78 and 84 can be reversed such that actuator shaft 78 would fit into second shaft tunnel 66 and actuator shaft 84 would fit into first shaft tunnel 64.

The operative association of carriage translation actuator 62 and carriage 50 includes coupling of actuator shaft 78 to follower shaft 84 to, in response to a rotational force applied to actuator shaft 78, rotate them in opposite directions and thereby move carriage 50 in either direction along the lengths of gear racks 72 and 76 to adjust the position of a medical probe over the surface of a patient's skin on which base 12 has been set and secured in place. Moreover, the coupling of actuator shaft 78 to follower shaft 84 provides essentially simultaneous engagement of first follower gear 86 and second follower gear 88, causing the gears to travel essentially equal distances along their respective racks thereby maintaining, relative to base 12, the spatial orientation of carriage 50 during adjustment. As shown in FIGS. 3A and 3B, first support portion 56 and second support portion 58 extend laterally in opposite directions from carriage 50 and are configured to fit into and move along respective first carriage guide surface 40 and second carriage guide surface 42 to facilitate a reproducible range of motion for carriage 50.

Figure 4A:
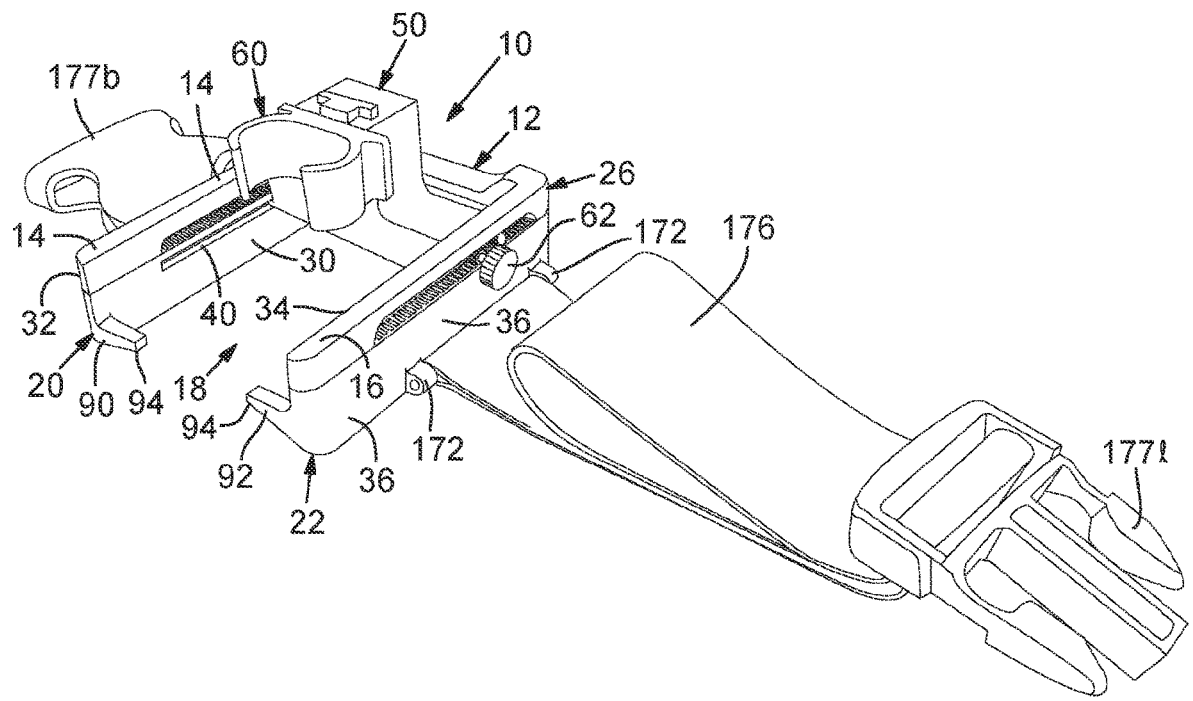
FIGS. 4A and 4B are, respectively, oblique front and back views of the disclosed guide structure showing first and second open ends of the base, having respective first and second bracing spurs, and first and second closed ends of the arms of the base.
Figure 4B:
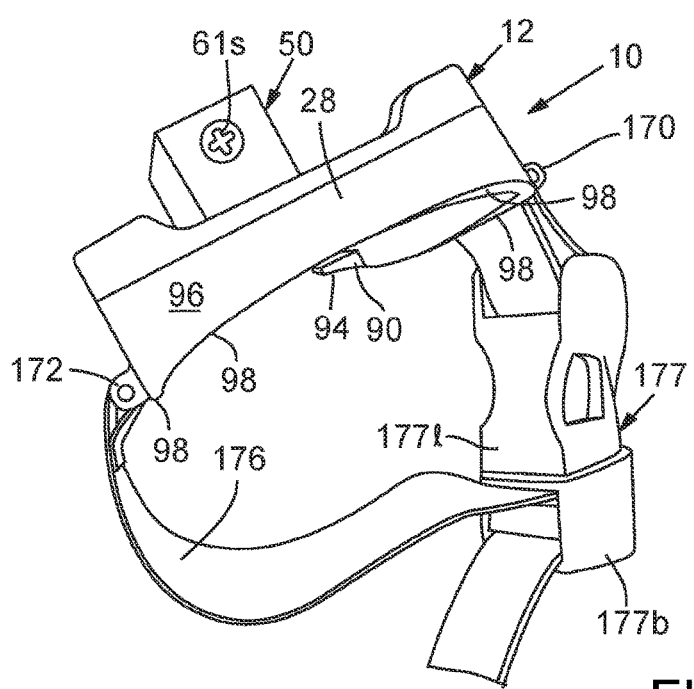

FIGS. 4A and 4B are, respectively, oblique front and back views of guide structure 10 showing first open end 20 and second open end 22 of base 12. In some embodiments, base 12 has a first bracing spur 90 and second bracing spur 92 positioned, respectively, on first arm 14 and second arm 16 of base 12 of guide structure 10 for impeding a patient's limb, neck, or torso from entering open space 18. In the embodiment shown in FIG. 4A, first bracing spur 90 and second bracing spur 92 are positioned at first open end 20 and second open end 22 of base 12 as shown in FIG. 4A. In other embodiments, first bracing spur 90 and second bracing spur 92 are positioned on, respectively, first interior surface 30 and second interior surface 34 of first arm 14 and second arm 16. In further embodiments, first bracing spur 90 and second bracing spur 92 have curved skin-facing aspects 94 for the contouring first bracing spur 90 and second bracing spur 92 to the surface of a patient's limb, neck, or torso. In an alternative embodiment, a third exterior surface 96 of medial section 28, first exterior surface 32, and second exterior surface 36 have a skin-facing friction portion 98 for securing guide structure 10 to the surface of a patient's limb, neck, or torso. Friction portion 98 can be, for example, a texture imparted, or a textured material adhered, to exterior surfaces 32, 36, and 96.

Figure 5:
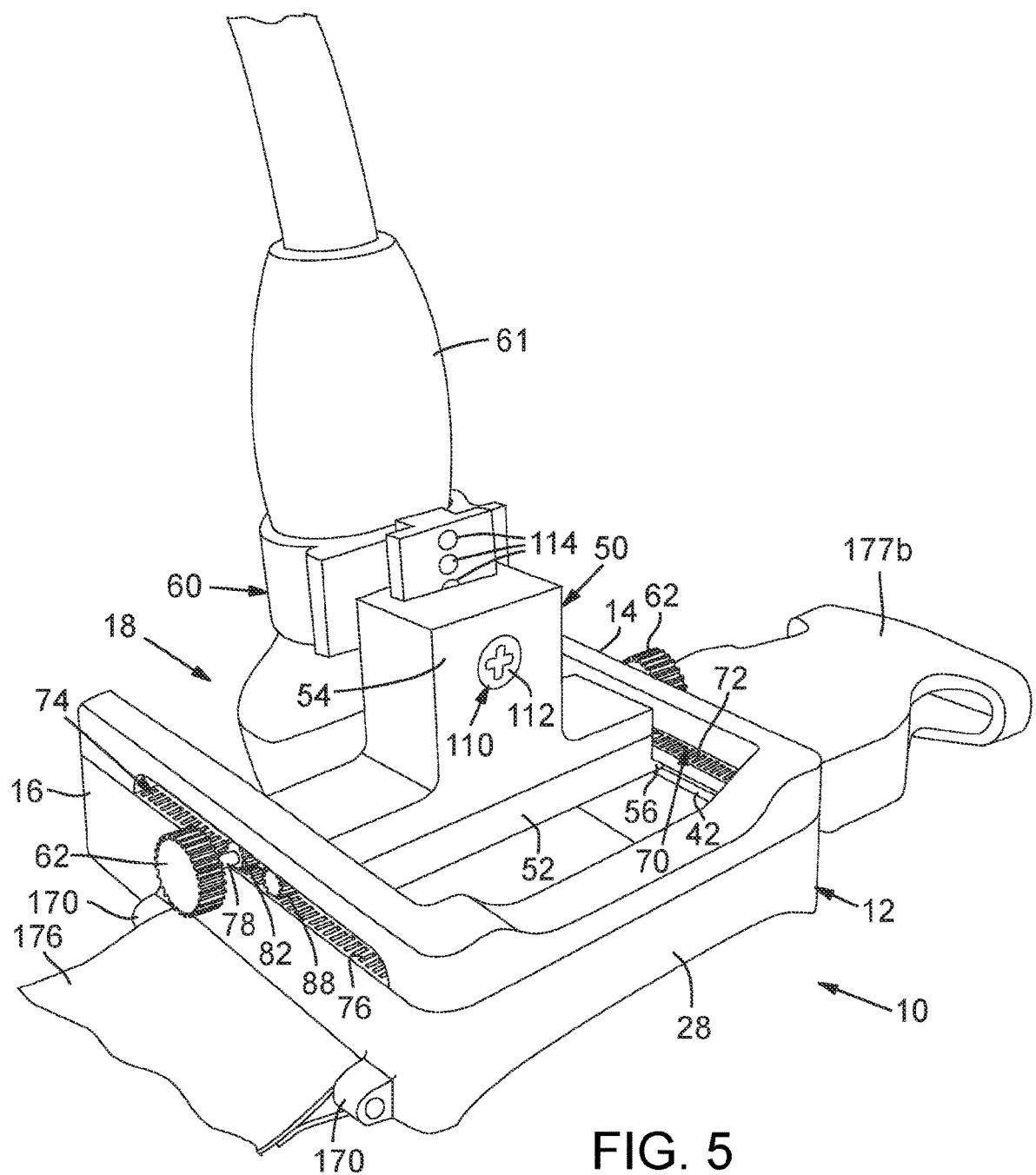
FIG. 5 is an oblique back-right side view of an alternative embodiment of the carriage post configured for operative association with a medical probe holder for adjusting the distance between the medical probe and the skin of a patient.

FIG. 5 is an oblique back-right side view of an alternative embodiment of carriage post 54 of carriage 50 configured for operative association with medical probe holder 60 for adjusting the distance between the medical probe and the skin of a patient. As shown in FIG. 5, carriage post 54 has a carriage post through-hole 110 configured to receive a carriage post fastener 112, such as a screw. Medical probe holder 60 along its length has a set of mutually spaced-apart hollows 114 positioned to selectively receive carriage post fastener 112 inserted into carriage post through-hole 110 to set, to a desired distance into open space 18, medical probe 61 placed in medical device holder 60.

Figure 6:
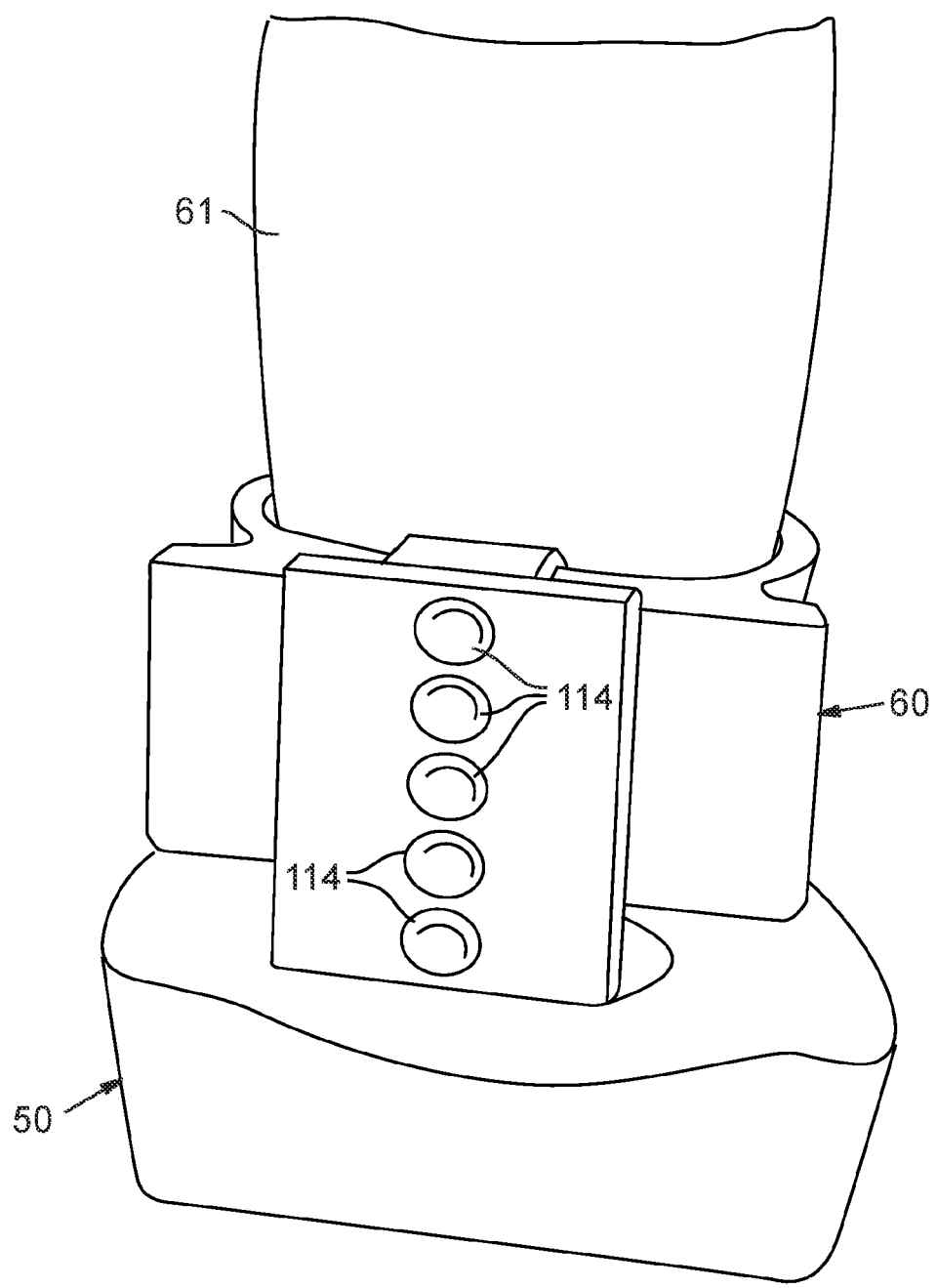
FIG. 6 is an enlarged fragmentary oblique view of an alternative embodiment of the medical probe holder of FIGS. 4A and 4B configured for positional adjustment with a carriage post.

FIG. 6 is a fragmentary oblique view of an alternative embodiment of medical probe holder 60 of FIG. 5. In the embodiment shown, mutually spaced-apart hollows 114 are positioned at discrete intervals along the length of medical device holder 60 to receive carriage post fastener 112 inserted into carriage post through-hole 110 and thereby provide for selective adjustment of the portion of medical probe 61 into open space 18 to a desired distance from the skin of the patient. In some embodiments, medical probe holder 60 is configured for about 0.5 centimeter to about 8.0 centimeters range of motion to set medical probe 61 placed in medical device holder 60 to a desired distance into open space 18.

Figure 7:
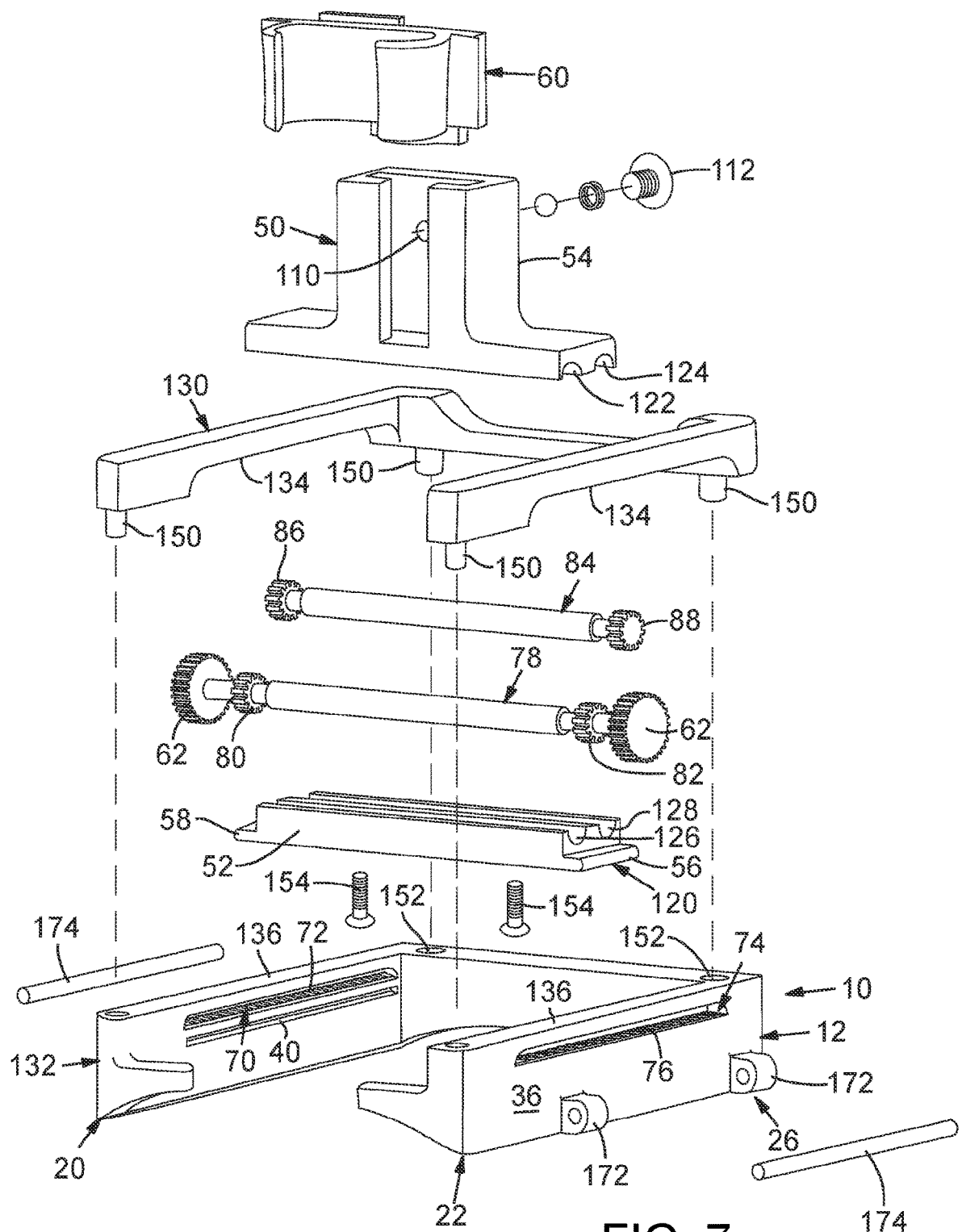
FIG. 7 is an exploded view of exemplary features of an alternative embodiment of the disclosed guide structure.

FIG. 7 is an exploded view showing the components of guide structure 10. In the embodiment shown, carriage 50 is an assembly of undercarriage 52 and carriage post 54, which are separate components that are fastened together in the manner described below. As shown in FIGS. 3A and 7, shaft tunnels 64 and 66 of carriage 50 include a first tunnel bisection 122 and a second tunnel bisection 124 formed and spaced apart from each other in carriage post 54, and a third tunnel bisection 126 and a fourth tunnel bisection 128 formed and spaced apart from each other in undercarriage 52. Third tunnel bisection 126 and fourth tunnel bisection 128 are spatially aligned with, and have complementary shape to, respective first tunnel bisection 122 and second tunnel bisection 124. Assembly of undercarriage 52 and carriage post 54 forms shaft tunnels 64 and 66 through which pass actuator shaft 78 and follower shaft 84, respectively. Base 12 is an assembly of an enclosure component 130 and a gearing component 132. Enclosure component 130 has in each of arms 14 and 16 a recessed portion forming in each of them an enclosure aspect 134 that is closed by a gearing aspect 136 of gearing component 132. A set of four enclosure pins 150 downwardly depending from open ends 20 and 22 and closed ends 24 and 26 of enclosure component 130 fits into a set of four blind holes 152 are formed at corresponding locations of gearing aspect 136 of gearing component 132 to form base 12. Undercarriage 52 and carriage post 54 are fastened together by a set of two screws 154, as shown in FIGS. 7 and 1B.

In some embodiments, first carriage adjustment channel 70 and second carriage adjustment channel 74 each measure about 1.0 centimeter to about 13.0 centimeters lengthwise between, respectively, first open end 20 and first closed end 24 of first arm 14 and second open end 22 and second closed end 26 of second arm 16. This range of carriage travel distance enables variable placement of medical probe 61 placed in medical probe holder 60 relative to the surface of a patient's skin, facilitating IV placement by a user. Variable placement of medical probe 61 allows a user attempting a IV placement to alternate between visualizing a patient's vein and a needle tip and thereby advance the needle tip in synchronism with medical probe 61 and to place the needle in the vein with less risk of injury to the patient. In another embodiment, medical probe holder 60 in carriage 50 of guide structure 10 is configured for about 0.5 centimeter to about 8.0 centimeters of sliding motion transverse to first arm 14 and second arm 16 for variable placement of medical probe 61 relative to the surface of a patient's limb, neck, or torso. This range of medical probe holder travel distance enables variable placement of medical probe 61 into open space 18, facilitating continuing contact of medical probe 61 with a patient's skin having surface irregularities as a needle tip and medical probe 61 are advanced in synchronism.

In an alternative embodiment, guide structure 10 includes a first restraint anchor 170 and a second restraint anchor 172 positioned on, respectively, the first exterior surface 32 and second exterior surface 36 of base 12 for supporting a limb restraint, a neck restraint, or a torso restraint. In another alternative embodiment, first restraint anchor 170 and second restraint anchor 172 are positioned proximal to, respectively, first closed end 24 and second closed end 26 of base 12 relative to first open end 20 and second open end 22. In some embodiments, an anchor rod 174 is coupled to each of first restraint anchor 170 and second restraint anchor 172 to couple a limb restraint 176 to guide structure 10 as shown in FIGS. 2A and 2B. The free ends of limb restraint 176 terminate in a side release buckle 177, which is shown in FIG. 4B. A body component 177b and a latch component 177l of side release buckle 177 are shown separated in FIG. 4A. Skilled persons will understand that limb restraint 176 may also be configured to function as a neck restraint or a torso restraint by adjusting the size of limb restraint 176 to encircle a patient's neck or torso.

Figure 8:
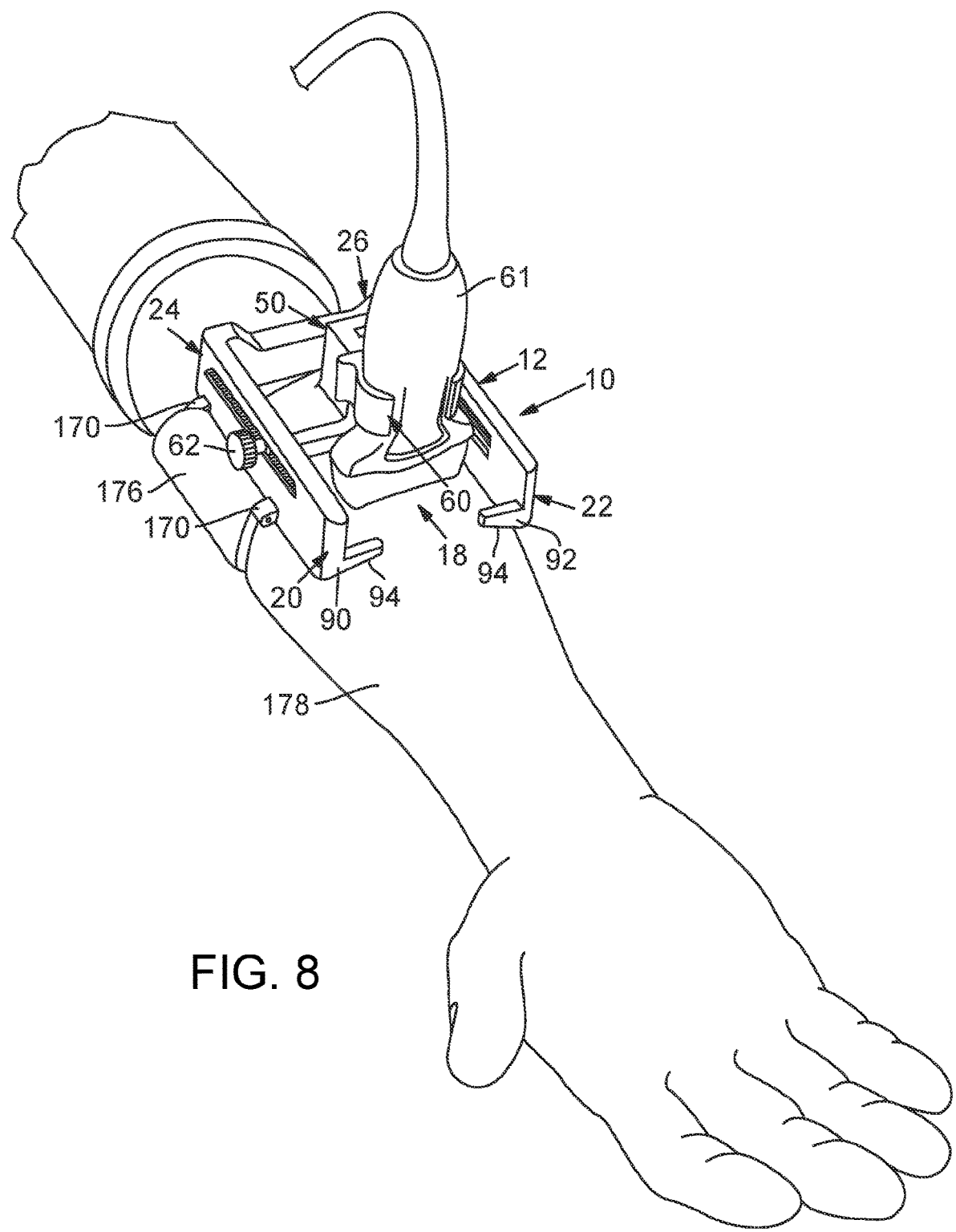
FIG. 8 is a fragmentary oblique view of an alternative embodiment of the guide structure secured to a patient skin for adjustable translation of a medical probe.

FIG. 8 is a fragmentary oblique view of a preferred embodiment of guide structure 10 secured to a patient's limb 178 for adjustable translation of medical probe 61. FIG. 8 shows a patient's arm as patient's limb 178, but guide structure 10 could also be placed on a patient's leg, neck, torso or other anatomy requiring an IV placement. In the embodiment shown, guide structure 10 is secured by a limb restraint supported by first restraint anchor 170 and second restraint anchor 172, and limb 178 is impeded from entering open space 18 of base 12 by first bracing spur 90 and second bracing spur 92. As shown in FIG. 1B and FIG. 8, first bracing spur 90 and second bracing spur 92 have curved skin-facing aspects 94 for facilitating fitting guide structure 10 to limb 178 of the patient. In some embodiments, medial section 28 has skin-facing friction portion 98 positioned on third exterior surface 96 for securing guide structure 12 to the surface of patient's limb 178, as shown in FIG. 1B. In other embodiments, first restraint anchor 170 and second restraint anchor 172 are positioned proximal to first closed end 24 and second closed end 26 of guide structure 10 relative to first open end 20 and second open end 22 to facilitate compression of patient's limb 178 at a location that is proximal relative to a needle insertion site.

Figure 9:
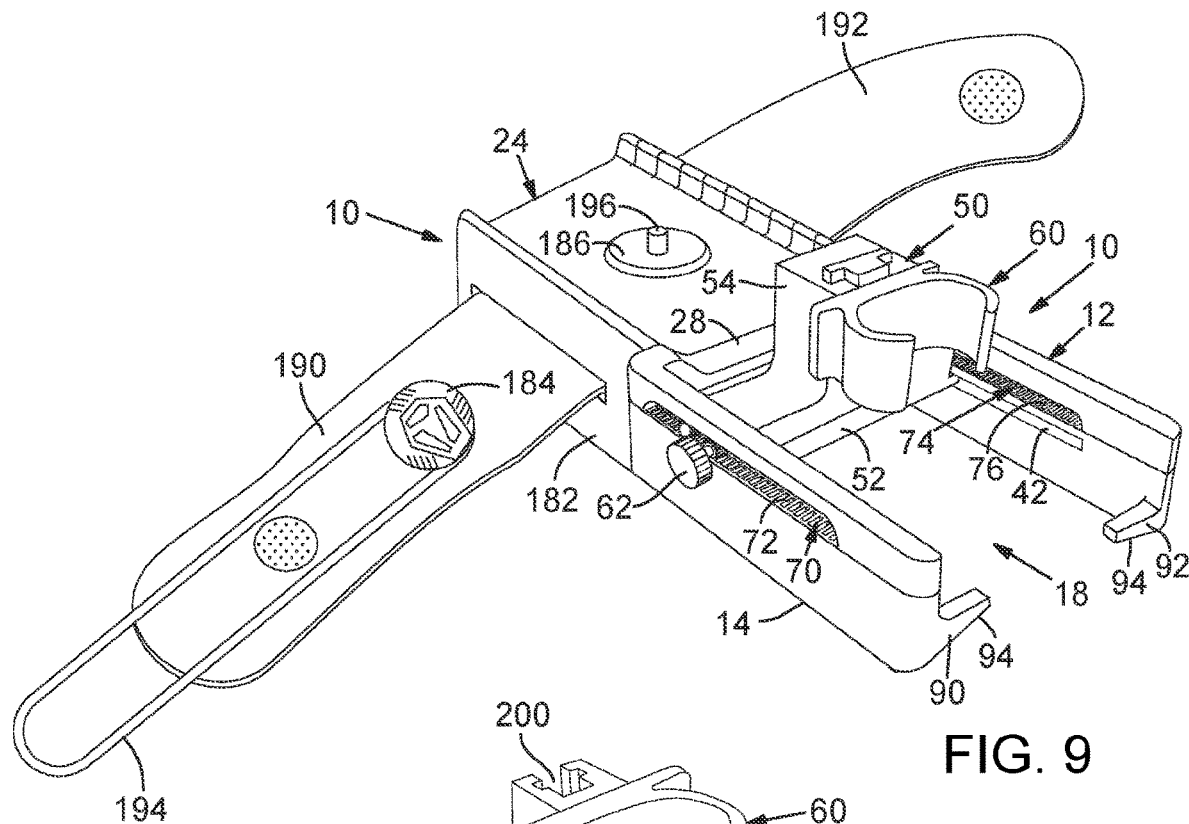
FIG. 9 is an oblique front-left side view of an alternative embodiment of the disclosed guide structure having a reel-based closure system for securing the guide structure to the skin of a patient.

FIG. 9 is an oblique front-left side view of an alternative embodiment of guide structure 10 having a reel-based restraint system 180 for securing guide structure 10 to a limb, neck, or torso of a patient. In the embodiment shown, restraint system 180 includes an extended base 182, a tightening spool 184, a release spool 186, with extended base 182 positioned on medial section 28 of base 12 and having a first limb restraint 190 and second limb restraint 192. A cable 196 is guided by tightening spool 184 and rotationally linked to release spool 186. In some embodiments, tightening spool 184 may be positioned on first limb restraint 190 or second limb restraint 192. In the embodiment shown, tightening spool 184 includes a manual control for manually winding a length of cable 194 around release spool 186 to tighten first limb restraint 190 and second limb restraint 192 around limb 178 of a patient. In the embodiment shown, a release actuator 196 is operatively connected to release spool 186 for selectively unwinding a length of cable 194 around release spool 186 to loosen first limb restraint 190 and second limb restraint 192 from limb 178 of a patient. One having ordinary skill in the will understand that first and second limb restraints 190 and 192 may also be configured to function as a neck restraint or a torso restraint by adjusting the size of first limb restraint 190 or second limb restraint 192 to encircle a patient's neck or torso.

Figure 10:
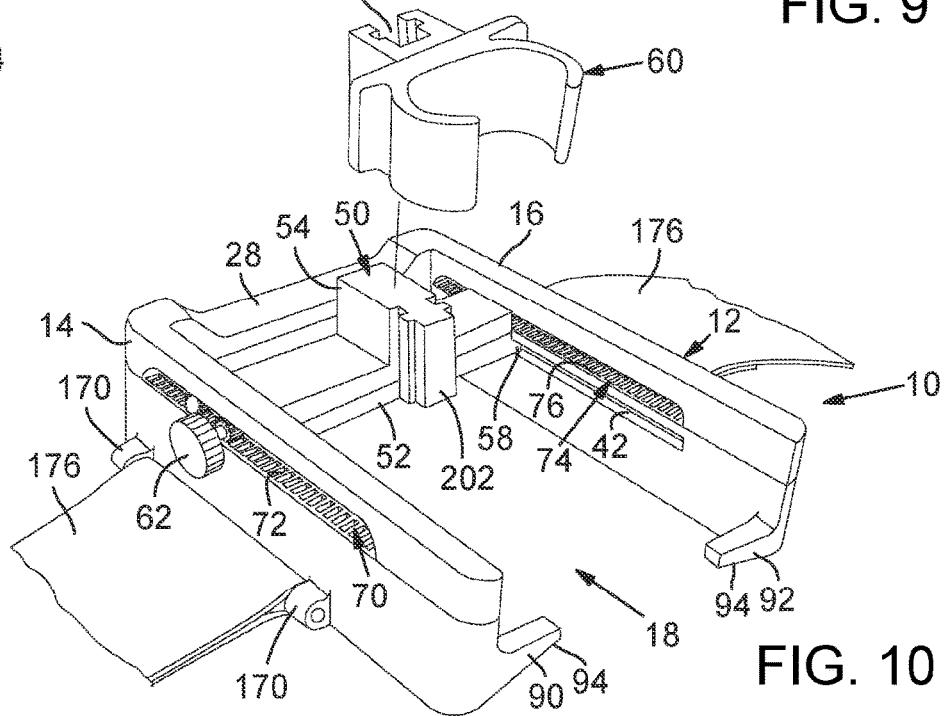
FIG. 10 is an oblique front-left side view of an alternative embodiment of the disclosed guide structure having a friction-fit based rail and bracket system for adjusting the position of the medical probe relative to the carriage.

FIG. 10 is an oblique front-left side view of an alternative embodiment of guide structure 10 having a friction-fit based rail and bracket system for adjusting the position of medical probe holder 60 relative to carriage 50. In the embodiment shown, medical probe holder 60 includes a notched rail bracket 200 that extends along the length of medical probe holder 60, and carriage post 54 includes a stepped guide rail 202 having a complementary shape to that of notched rail bracket 200. Guide rail 202 and rail bracket 200 form a friction fit to set, in non-discrete increments to a desired distance into open space 18 separating first arm 14 and second arm 16, medical probe 61 placed in medical probe holder 60.

Figure 11:
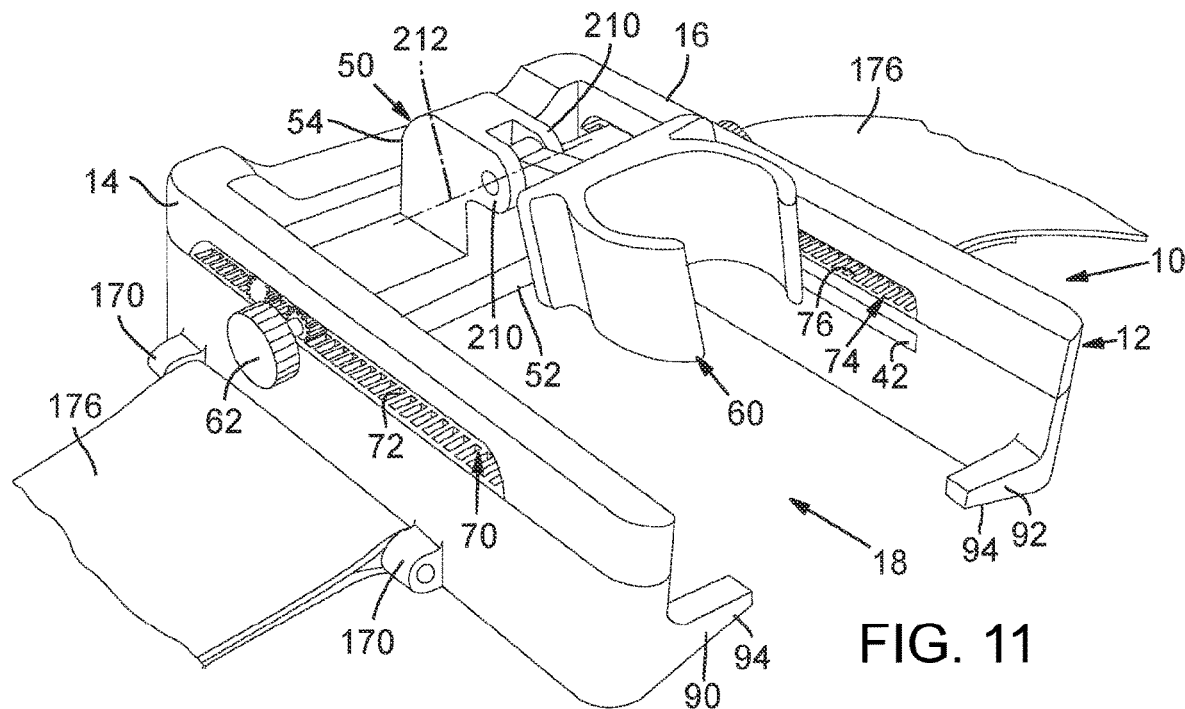
FIG. 11 is an oblique front-left view of an alternative embodiment of the disclosed guide structure having a mounting arm to which the medical probe holder is pivotally connected for movement about a pivot axis.

FIG. 11 is an oblique front-left side view of an alternative embodiment of guide structure 10, in which carriage post 54 has a mounting arm 210 that is pivotally connected at its distal end to medical probe holder 60 for movement about a pivot axis 212. In the embodiment shown, medical probe holder 60 is movable about pivot axis 212 in a direction generally transverse to first and second arms 14 and 16 of base 12 to facilitate fitting medical probe 61 placed in medical probe holder 60 against the surface of the patient's limb, neck, or torso.

Figure 12:
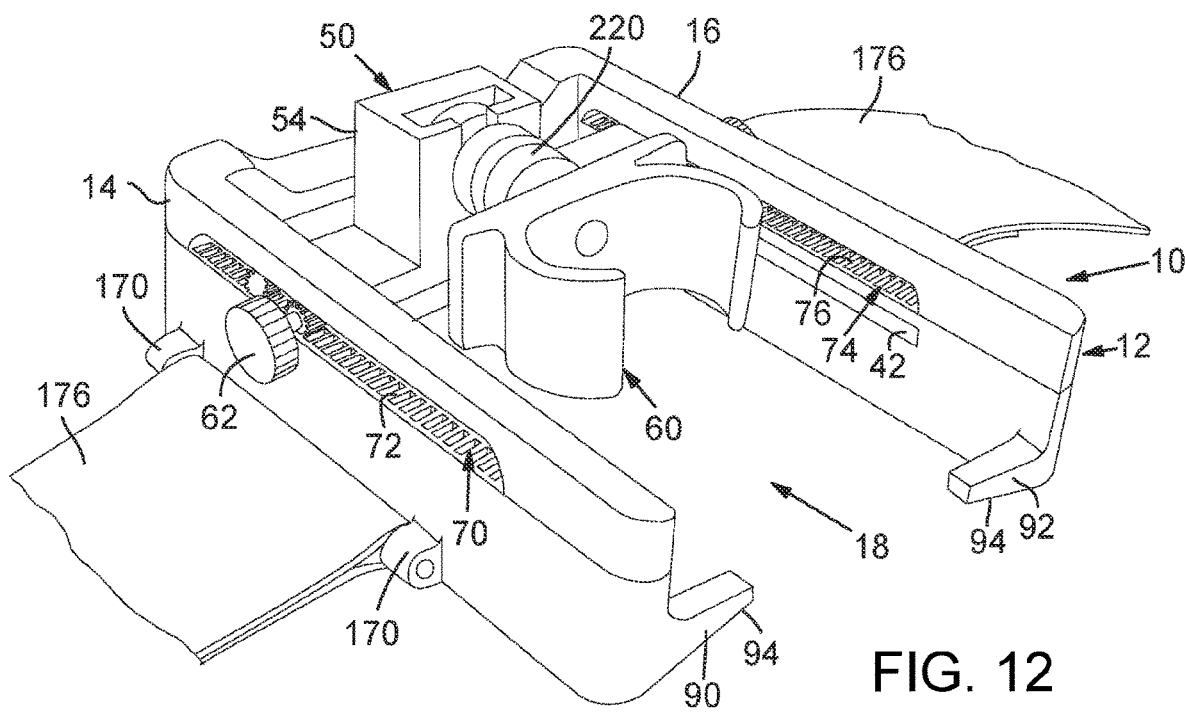
FIG. 12 is an oblique front-left side view of an alternative embodiment of the disclosed guide structure linked to a medical probe holder by an elastomeric spring.

FIG. 12 is an oblique front-left side view of an alternative embodiment of guide structure 10 having a medical probe holder 60 that is coupled to carriage post 54 by an elastomeric spring 220. In the embodiment shown, elastomeric spring 220 imparts a naturally restorative force to medical probe 61 placed in medical probe holder 60. The naturally restorative force of elastomeric spring 220 facilitates Vernier-based adjustments to the position of medical probe 61 and thereby maintain continuing contact of medical probe 61 with the surface of the patient's limb, neck, or torso.

"Medical grade" is a class of materials and polymers, including plastics, silicone, and rubber, designed and manufactured to be biocompatible and not compromise patient safety. Medical grade also indicates the capacity for devices that incorporate medical grade polymers to be sterilized without affecting the performance of the device. In the embodiments disclosed, the guide structure is preferably sterilized prior to use.

Medical-grade plastic may include acrylonitrile butadiene styrene (ABS) polyethylene, polylactic acid (PLA), polypropylene, polystyrene, polyester, polycarbonate, polyvinyl chloride, polyesther sulfone, polyacrylate, acrylate, polysulfone, polyetheretherketone, thermoplastic elastomer, thermoset elastomer (silicone), poly-p-xylylene, or fluoropolymer.
In some embodiments, guide structure 10 is made of medical grade materials to facilitate sterilization of guide structure 10 prior to use. In some embodiments, guide structure 10 is made of polylactic acid to allow guide structure 10 to be biodegradable. In some embodiments, guide structure 10 is manufactured using an additive manufacturing process (e.g., 3D-printing technology) to selectively fabricate one-piece components of guide structure 10. For example, base 12 may be manufactured having enclosure component 130 and gearing component 132 fused together. In another example, carriage 50 may be manufactured having undercarriage 52 and carriage post 54 fused together, with actuator shaft 78 or follower shaft 84 being placed into either first shaft tunnel 64 or second shaft tunnel 66 after a one-piece carriage 50 is fabricated.

EXAMPLES

The following examples further describe and demonstrate use of preferred embodiments of the disclosed guide structure 10. The example is given solely for the purpose of illustration and is not to be construed as limiting use of guide structure 10 because many variations thereof are possible without departing from the spirit and scope of uses of guide structure 10. These examples demonstrate the benefits guide structure to hold a medical probe and adjustably position it over a region of a surface of a patient's limb.

Example 1—Leaf-Spring Based Carriage Translation Actuator

Figure 13A:
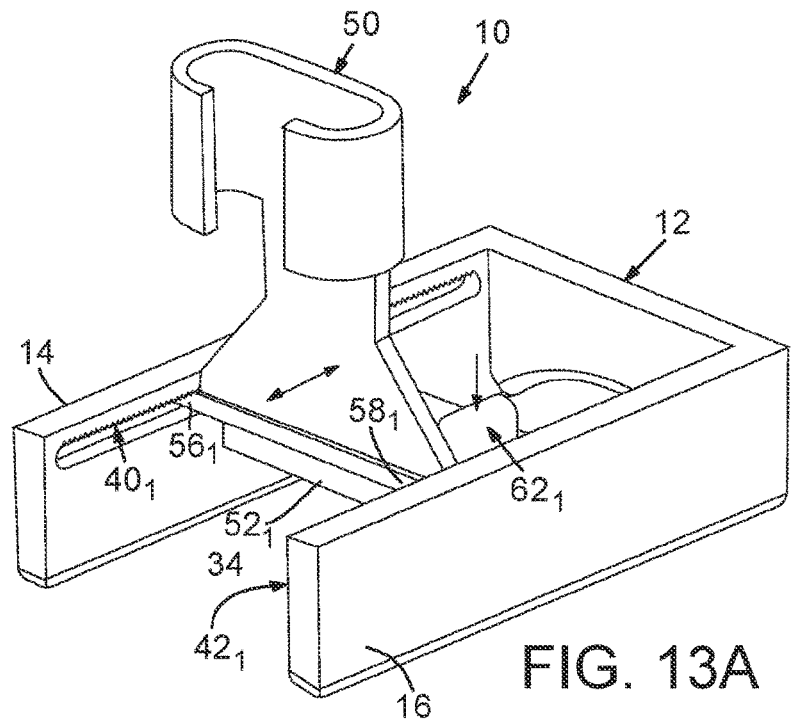
FIG. 13A is an oblique front-right side view of an alternative embodiment of the disclosed guide structure having a leaf-spring based carriage translation actuator in operative association with the undercarriage to facilitate moving and adjusting the carriage.

FIG. 13A is an oblique front-right side view of an alternative embodiment of guide structure 10, in which a leaf-spring based carriage translation actuator $62_1$ is in operative association with an undercarriage $52_1$ to facilitate moving and adjusting a carriage $50_1$. As shown in FIG. 13A, carriage translation actuator $62_1$ may be pressed and released by a user to selectively engage or disengage a first support portion $56_1$ and a second support portion $58_1$ of undercarriage $52_1$ to or from, respectively, a first carriage guide surface $40_1$ extending along first arm 14, and a second carriage guide surface $42_1$ extending along second arm 16 to move and adjust carriage $50_1$ relative to base 12. In some embodiments, a leaf-spring mechanism may bias carriage $50_1$ to engage base 12 and hold carriage $50_1$ in contact with the guide surfaces. In some embodiments, the engagement is a friction fit. In some embodiments, the engagement is enhanced by guide surfaces having serrations or "teeth" to increase the friction between the guide surfaces and the carriage $50_1$. A user may disengage the carriage by pressing on carriage translation actuator $62_1$ to disengage carriage $50_1$ from first carriage guide surface $40_1$ and second carriage guide surface $42_1$, freeing carriage $50_1$ to be moved and adjusted by a user.

Figure 13B:
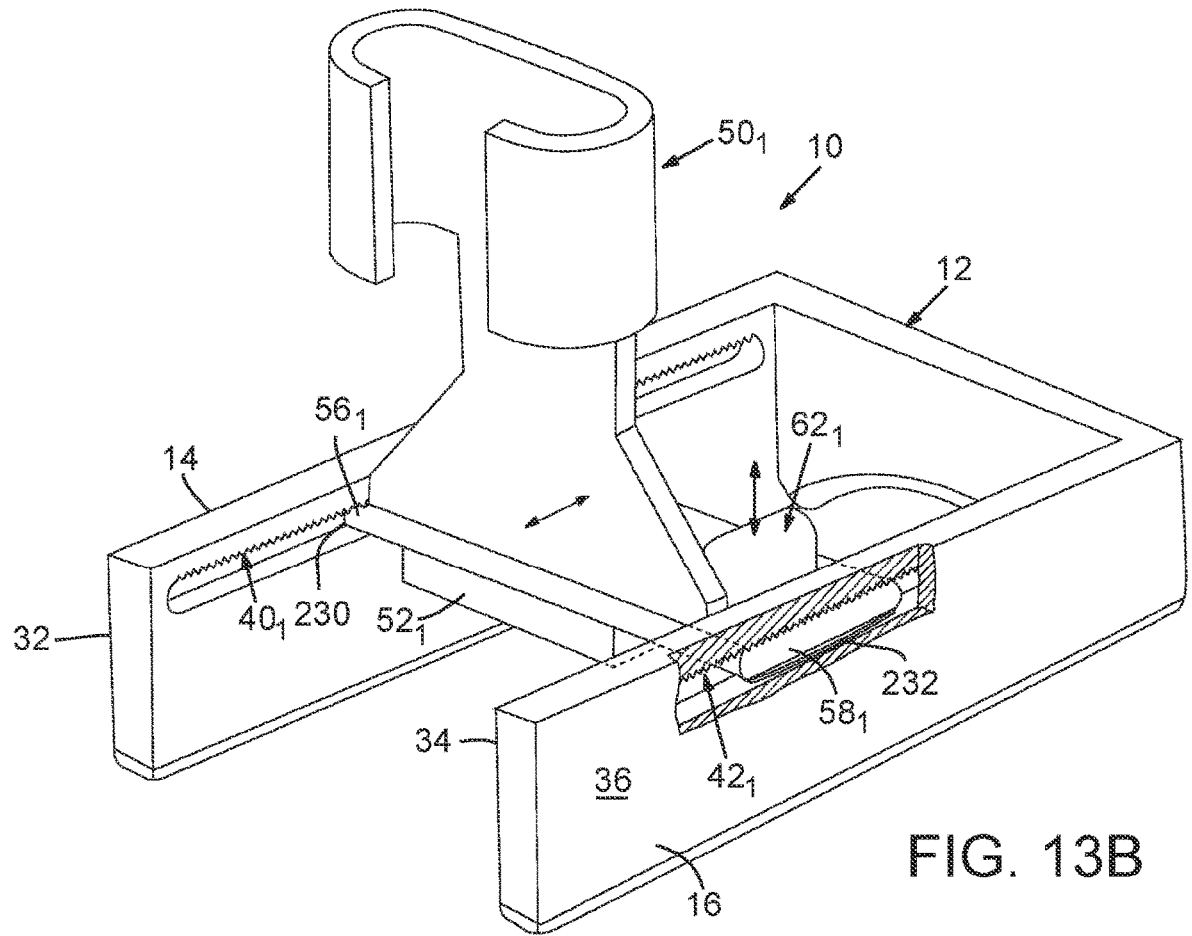
FIG. 13B is an enlarged oblique front-right side sectional view of the carriage translation actuator of the guide structure of FIG. 13A with a portion cut away to show a leaf spring in operative association with the undercarriage to form a friction fit to the base to secure the carriage in place.

FIG. 13B is an enlarged oblique front-right side sectional view showing carriage translation actuator $62_1$ of the guide structure of FIG. 13A with a portion of interior surface 30 cut away to show a leaf spring 230 positioned underneath first support portion $56_1$ and a portion of exterior surface 36 cut away to show a leaf spring 232 positioned beneath second support portion $58_1$ of undercarriage $52_1$. First support portion $56_1$ and second support portion $58_1$ are biased to engage, respectively, first carriage guide surface $40_1$ and second carriage guide surface $42_1$ by first leaf spring 230 and second leaf spring 232 of base 12 to create a friction fit and secure carriage $50_1$ in place. In the embodiment shown in FIG. 13B, first carriage guide surface $40_1$ and second carriage guide surface $42_1$ are serrated to enhance the friction fit.

Example 2—Screw-Drive Based Carriage Translation Actuator

Figure 14A:
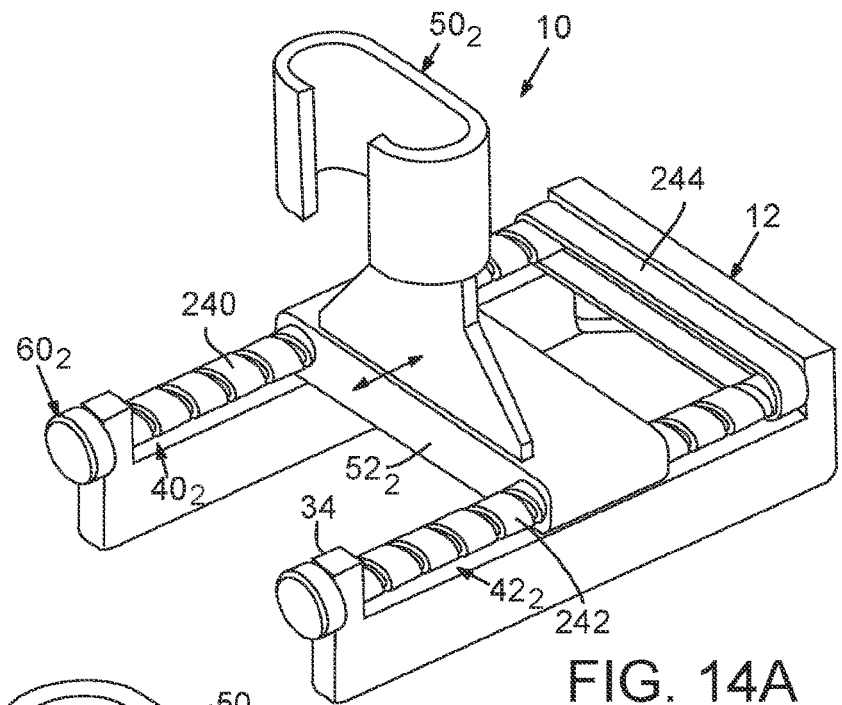
FIG. 14A is an oblique front-right side view of an alternative embodiment of the disclosed guide structure having a screw-drive based carriage translation actuator in operative association with the undercarriage to facilitate moving and adjusting the carriage.

FIG. 14A is an oblique front-right side view of an alternative embodiment of guide structure 10, in which a screw-drive based carriage translation actuator $62_2$ is in operative association with an undercarriage $52_2$ to facilitate moving and adjusting a carriage $50_2$. As shown in FIG. 14A, a user may apply a rotational force to carriage translation actuator $62_2$ to rotate a first screw drive 240 and a second screw drive 242 interconnected by a belt 244 to move and adjust undercarriage $52_2$ along a first carriage guide surface $40_2$ and a second carriage guide surface $42_2$ of base 12. As shown in FIG. 14A, a screw drive moves carriage $50_2$ along first and second carriage guide surfaces $40_2$ and $42_2$ relative to base 12. First screw drive 240 and second screw drive 242 are interconnected by belt 244 to facilitate positive displacement. In some embodiments, belt 244 is a belt drive. Skilled persons will understand that other drive mechanisms may achieve the same positive displacement as belt 244.

Figure 14B:
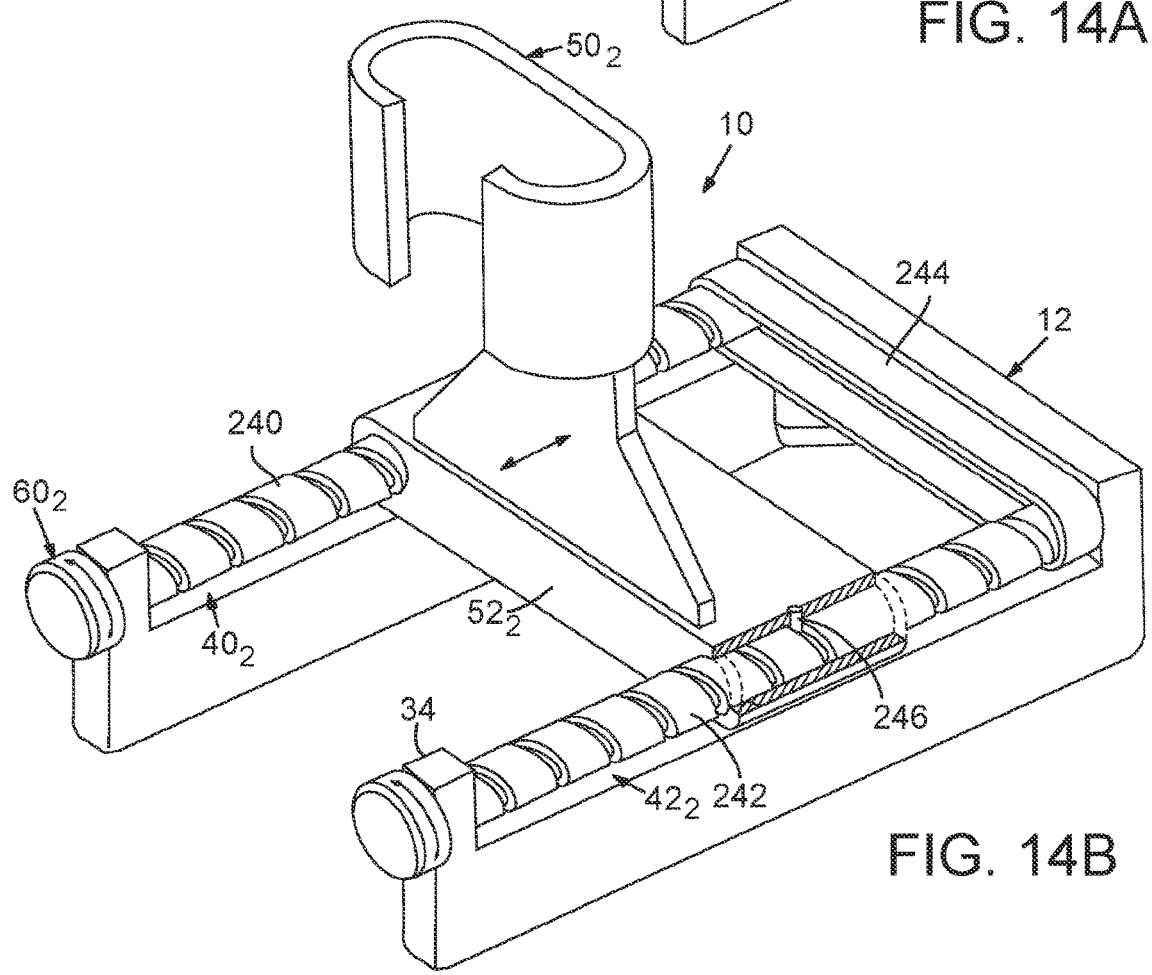
FIG. 14B is an enlarged oblique front-right side sectional view of the carriage translation actuator of the guide structure of FIG. 14A with a portion cut away to show a screw drive in operative association with an internal guide pin to constrain the motion of the carriage.

FIG. 14B is an enlarged oblique front-right side sectional view of carriage translation actuator $62_2$ of the guide structure of FIG. 14A with a portion of the surface of undercarriage $52_2$ cut away to show second screw drive 242 in operative association with a second internal guide pin 246 of undercarriage $52_2$ to constrain the motion of second screw drive 242. In some embodiments, a first internal guide pin (not shown) and second internal guide pin 246 are connected to undercarriage $52_2$ to constrain the motion of, respectively, first screw drive 240 and second screw drive 242. As shown in FIG. 14B, second internal guide pin 246 is set in the thread of second screw drive 242 to constrain its motion and facilitate accurate displacement of carriage $50_2$. In some embodiments, the pitch of the screw drives may be configured for fine or coarse movement.

Example 3—Thumbwheel Based Carriage Translation Actuator

Figure 15A:
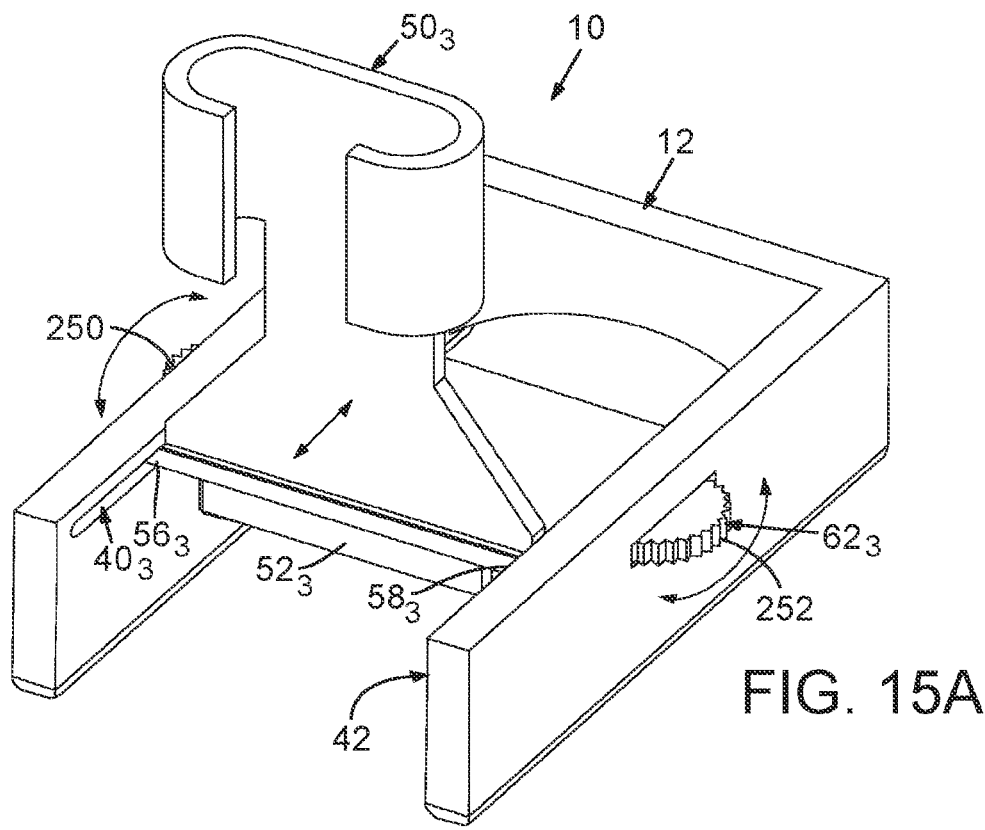
FIG. 15A is an oblique front-right side view of an alternative embodiment of the disclosed guide structure having a thumbwheel-based carriage translation actuator in operative association with the undercarriage to facilitate moving and adjusting the carriage.

FIG. 15A is an oblique front-right side view of an alternative embodiment of guide structure 10, in which a thumbwheel based carriage translation actuator $62_3$ is in operative association with an undercarriage $52_3$ to facilitate moving and adjusting a carriage $50_3$ by selectively rotating a first thumbwheel 250 and a second thumbwheel 252 to move and adjust carriage $50_3$ along a first carriage guide surface $40_3$ and a second carriage guide surface $42_3$ relative to base 12. In some embodiments, a first support portion $56_3$ and a second support portion $58_3$ of undercarriage $52_3$ each comprise one or more support pins (not shown) to constrain the movement of carriage $50_3$ along first carriage guide surface $40_3$ and second carriage guide surface $42_3$.

Figure 15B:
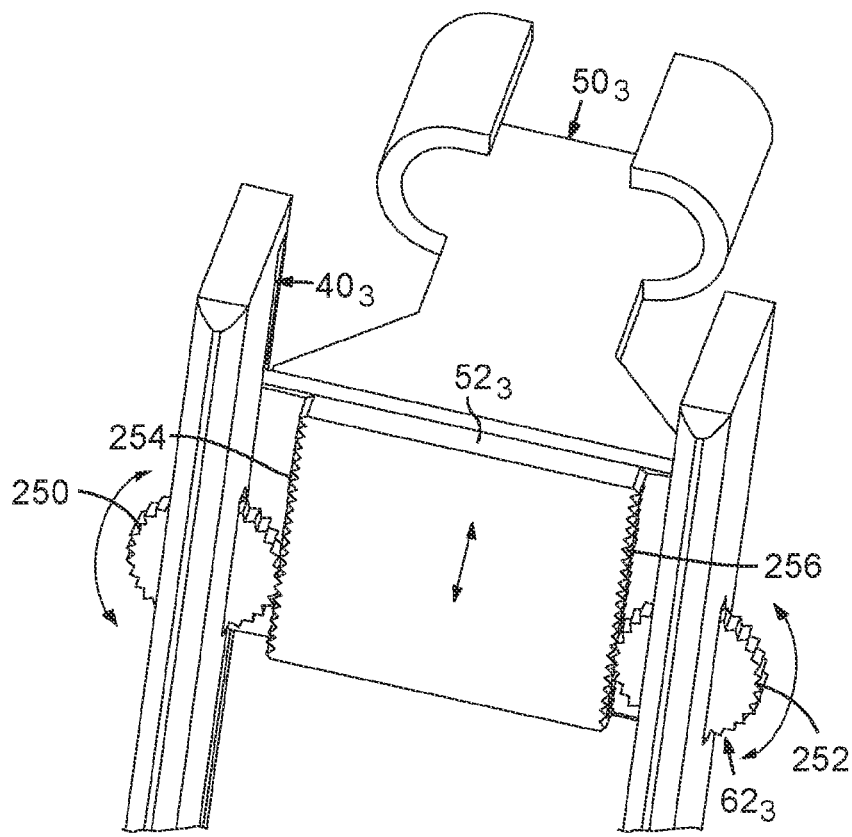
FIG. 15B is an oblique front-right bottom view showing thumbwheels of the carriage translation actuator of the guide structure of FIG. 15A in operative association with the undercarriage to move and adjust the carriage.

FIG. 15B is an oblique front-right bottom view showing thumbwheels 250 and 252 of carriage translation actuator $62_3$ of the guide structure of FIG. 15A in operative association with undercarriage $52_3$ to move and adjust carriage $50_3$. As shown in FIG. 15B, first thumbwheel 250 and second thumbwheel 252 are set to mesh with, respectively, a first thumbwheel gear rack 254 and a second thumbwheel rack 256 formed on undercarriage $52_3$ whereby an application of a rotational force to first thumbwheel 250 and second thumbwheel 252 moves and adjusts carriage $50_3$.

Example 4—Horizontally Oriented Thumbwheel-Based Carriage Translation Actuator

Figure 16A:
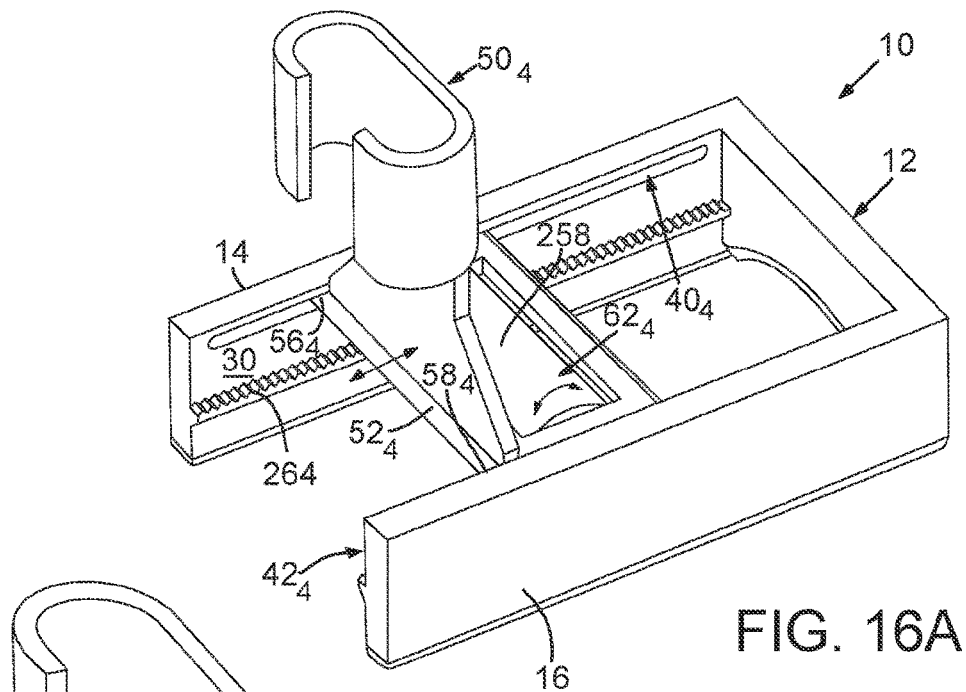
FIG. 16A is an oblique front-right side view of an alternative embodiment of the disclosed guide structure having a thumbwheel-based carriage translation actuator in operative association with an undercarriage and having thumbwheel gears set to mesh with thumbwheel gear racks formed on, the interior surfaces to facilitate moving and adjusting the carriage along the first and second carriage guide surfaces of the base.

FIG. 16A is an oblique front-right side view of an alternative embodiment of guide structure 10, in which a horizontally oriented (i.e., it moves about a pivot axis generally transverse to first arm 14 and second arm 16) thumbwheel-based carriage translation actuator $62_4$ is in operative association with an undercarriage $52_4$ and having a horizontal thumbwheel 258 to facilitate moving and adjusting a carriage $50_4$ by selectively rotating horizontal thumbwheel 258 to move first and second support portions $56_4$ and $58_4$ of undercarriage $52_4$ along a first carriage guide surface $40_4$ and a second carriage guide surface $42_4$ of base 12.

Figure 16B:
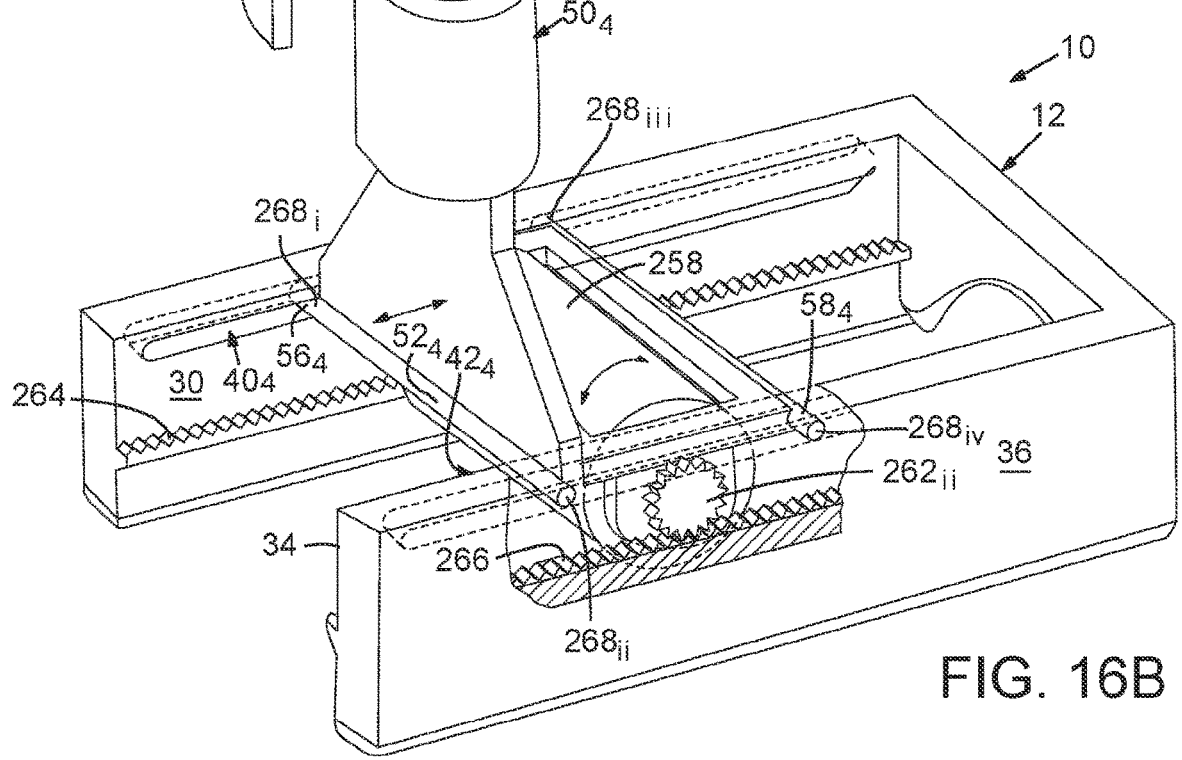
FIG. 16B is an enlarged oblique front-right side view showing a thumbwheel gear of the guide structure of FIG. 16A set to mesh with a thumbwheel gear rack to engage with the base and, in response to rotational force applied to the thumbwheel, selectively move and adjust the carriage.

FIG. 16B is an enlarged oblique front-right side view of the guide structure of FIG. 16A with phantom lines and a portion of exterior surface 36 cut away to show a thumbwheel gear of horizontal thumbwheel 258 set to mesh with a thumbwheel gear rack to engage with base 12 and, in response to rotational force applied to horizontal thumbwheel 258, selectively move and adjust carriage $50_4$. As shown in FIG. 16B, a first thumbwheel gear (not shown) and a second thumbwheel gear $262_{ii}$ are formed on opposing ends of horizontal thumbwheel 258 and are set to mesh with, respectively, a first thumbwheel gear rack 264 and a second thumbwheel gear rack 266. In the embodiment shown in FIG. 16B, first thumbwheel rack 264 and second thumbwheel rack 266 are formed on, respectively, first interior surface 30 and second interior surface 34. Skilled persons will understand that the gear teeth of thumbwheels gears and thumbwheel gear racks may be sized for greater or lesser incremental motion.

In some embodiments, first support portion $56_4$ and a second support portion $58_4$ of undercarriage $52_4$ each comprise one or more support pins 268 to constrain the movement of carriage $50_4$ along first carriage guide surface $40_3$ and second carriage guide surface $42_3$. As shown in FIG. 16B, first and third support pins $268_i$ and $268_{iii}$ of first support portion $56_4$ and second and fourth support pins $268_{ii}$ and $268_{iv}$ of second support portion $58_4$ are set in, respectively, first and second carriage guide surfaces $40_4$ and $42_4$ to constrain the movement of undercarriage $52_4$ and secure carriage $50_4$ to base 12.

Example 5—Compliance-Wheel Based Carriage Translation Actuator

Figure 17A:
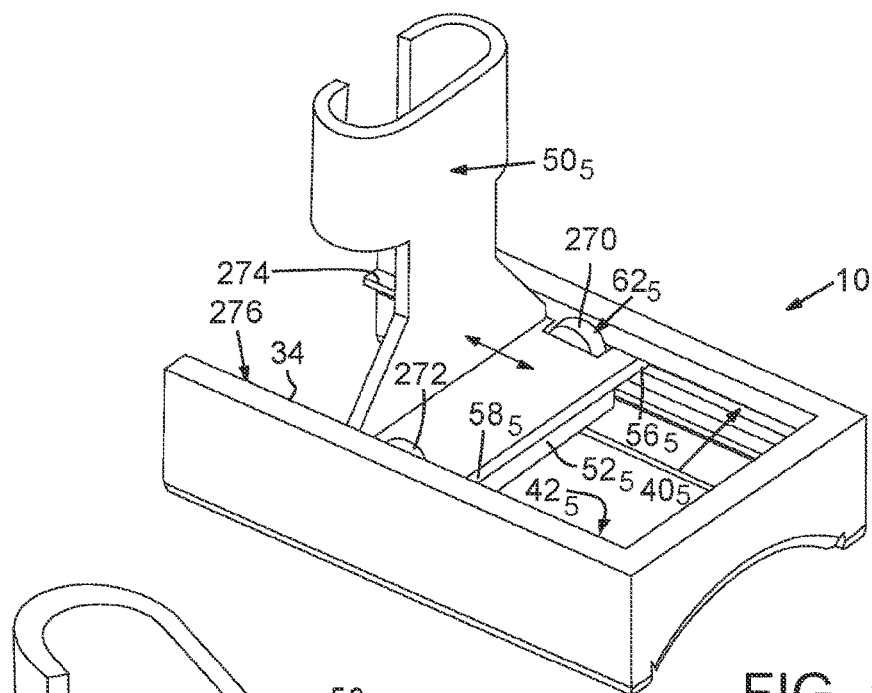
FIG. 17A is an oblique rear-right side view of an alternative embodiment of the disclosed guide structure having a compliant-wheel based carriage translation actuator in operative association with an undercarriage having elastomeric compliant wheels set to create rolling resistance with compliant wheel surfaces formed on the interior surfaces of the base to facilitate moving and adjusting the carriage.

FIG. 17A is an oblique rear-right side view of an alternative embodiment of guide structure 10, in which a compliance-wheel based carriage translation actuator $62_5$ is in operative association with an undercarriage $52_5$. As shown in FIG. 17A, undercarriage $52_5$ has a first elastomeric compliant wheel 270 and a second elastomeric compliant wheel 272 set to create rolling resistance with, respectively, a first compliant wheel surface 274 and a second compliant wheel surface 276 to facilitate moving and adjusting a carriage $50_5$ by selectively applying an external longitudinal force to undercarriage $52_5$ to overcome the rolling resistance of first and second compliant wheels 270 and 272.

Figure 17B:
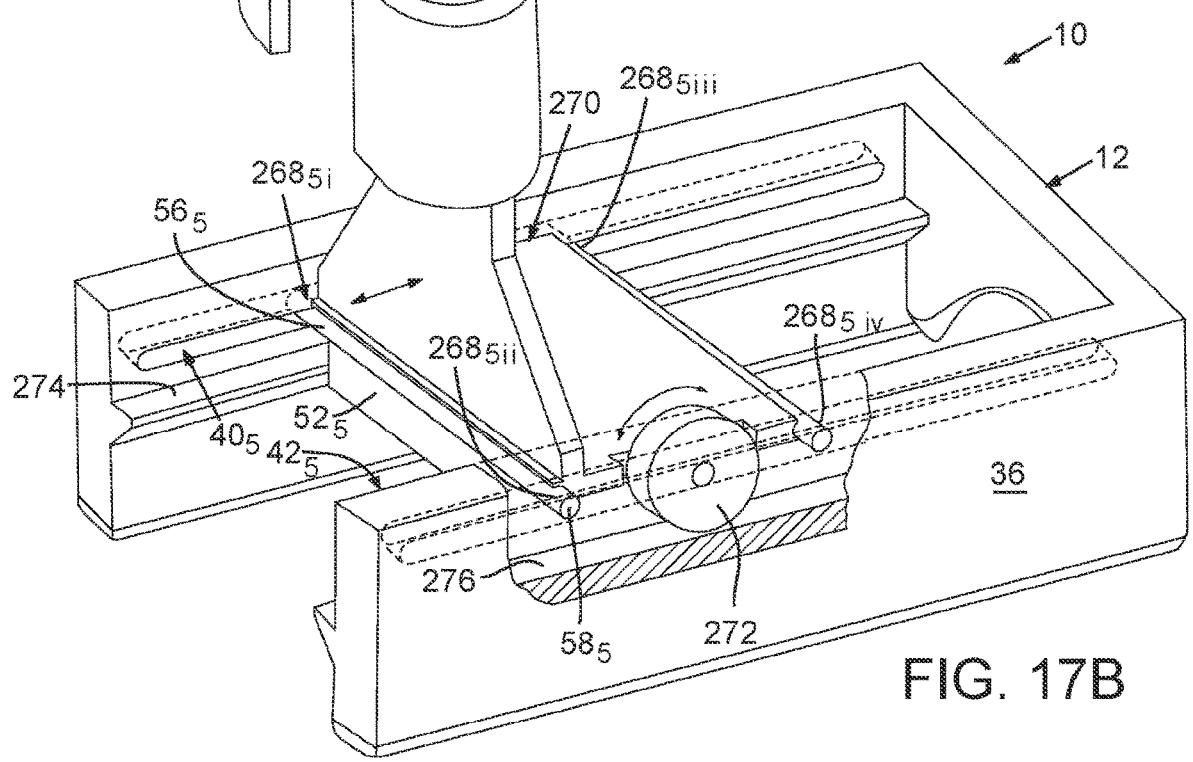
FIG. 17B is an enlarged oblique front-right side sectional view showing a compliant wheel of the guide structure of FIG. 17A with phantom lines and a portion cut away to show a compliant wheel engaged with a compliant wheel surface to create rolling resistance (i.e., an "interference fit") and secure the carriage to the base until an external longitudinal force is applied to the carriage to overcome the rolling resistance of the compliant wheels and thereby move and adjust the carriage.

FIG. 17B is an enlarged oblique front-right side sectional view of the guide structure of FIG. 17A with phantom lines and a portion of exterior surface 36 cut away to show second compliant wheel 272 engaged with second compliant wheel surface 276 to create rolling resistance (i.e., an "interference fit") and secure carriage $50_5$ to base 12 until an external longitudinal force is applied to carriage $50_5$ to overcome the rolling resistance of first and second compliant wheels 270 and 272 to move and adjust carriage $50_5$. As shown in FIG. 17B, flexible elastomeric wheels 270 and 272 deform under pressure from rolling resistance to create an interference fit that, when no external forces are applied, holds carriage $50_5$ in place.

In some embodiments, a first support portion $56_5$ and a second support portion $58_5$ of undercarriage $52_5$ each comprise one or more support pins 268 to constrain the movement of carriage $50_5$ along first carriage guide surface $40_5$ and second carriage guide surface $42_5$. As shown in FIG. 17B, first and third support pins $268_{5i}$ and $268_{5iii}$ of first support portion $56_5$ and second and fourth support pins $268_{5ii}$ and $268_{5iv}$ of second support portion $58_5$ are set in, respectively, first and second carriage guide surfaces $40_5$ and $42_5$ to constrain the movement of undercarriage $52_5$ and secure carriage $50_5$ to base 12. In some embodiments, the support pins may be configured to adjust the level of rolling resistance or interference fit.

Example 6—Pinned Lever-Arm Based Carriage Translation Actuator

Figure 18A:
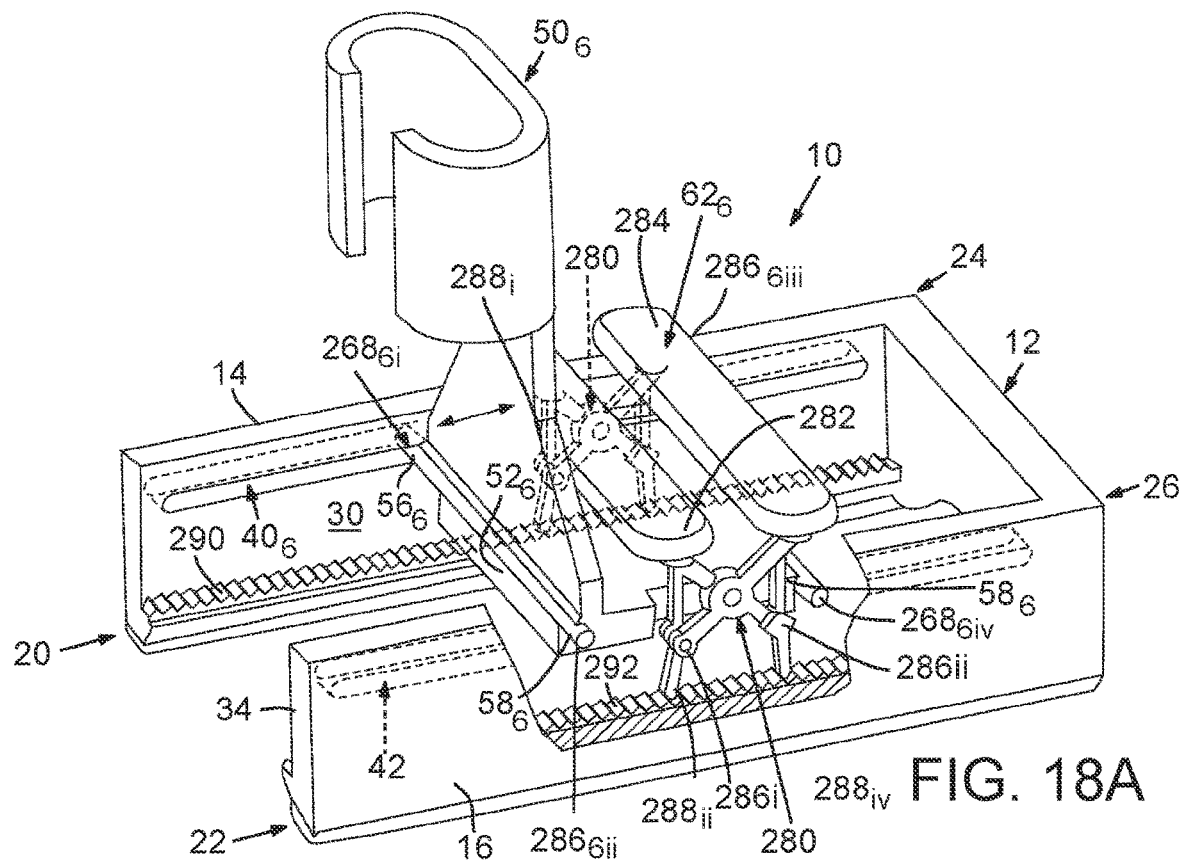
FIG. 18A is an oblique front-left side view of an alternative embodiment of the disclosed guide structure having a pinned lever-arm based carriage translation actuator in operative association with the undercarriage to facilitate moving and adjusting the carriage of the guide structure along the carriage guide surfaces of the base.

FIG. 18A is an oblique front-left side view of an alternative embodiment of guide structure 10, in which a pinned lever-arm based carriage translation actuator $62_6$ is in operative association with an undercarriage $52_6$ to facilitate moving and adjusting a carriage $50_6$ along first and second carriage guide surfaces $40_6$ and $42_6$ of base 12. As shown in FIG. 18A, a pinned lever-arm mechanical assembly 280 has a first lever arm 282 and a second lever arm 284 interconnected by a set of one or more lever knees 286 to a set of one or more spring-lock legs 288. In some embodiments, spring-lock legs 288 selectively engage and disengage first and second lever racks 290 and 292 formed on, respectively, first interior surface 30 of first arm 14 and second interior surface 34 of second arm 16 to facilitate moving and adjusting carriage $50_6$ along first carriage guide surface $40_6$ and second carriage guide surface $42_6$.

As shown by a portion of exterior surface 36 cut away in FIG. 18A, first and third spring-lock legs $288i$ and $288_{iii}$ are engaged with first lever rack 290 and second and fourth spring-lock legs $288_{ii}$ and $288_{iv}$ are engaged with second lever rack 292 in a "locked" configuration to maintain engagement with base 12 and facilitate holding carriage $50_6$ in place relative to base 12. In some embodiments, applying pressure to first lever arm 282 frees third and fourth spring-lock legs $288_{iii}$ and $288_{iv}$, allowing carriage $50_6$ to move towards first and second closed ends 24 and 26 of base 12. In some embodiments, applying pressure to second lever arm 284 frees first and second spring-lock legs $288_i$ and $288_{ii}$ allowing carriage $50_6$ to move towards first and second open ends 20 and 22 of base 12.

In some embodiments, first support portion $56_6$ and a second support portion $58_6$ of undercarriage $52_6$ each comprise one or more support pins 268 to constrain the movement of carriage $50_6$ along first carriage guide surface $40_6$ and second carriage guide surface $42_6$. As shown in FIG. 16B, first and third support pins $268_{6i}$ and $268_{6iii}$ of first support portion $56_6$ and second and fourth support pins $268_{6ii}$ and $268_{6iv}$ of second support portion $58_6$ are set in, respectively, first and second carriage guide surfaces $40_6$ and $42_6$ to constrain the movement of undercarriage $52_6$ and secure carriage $50_6$ to base 12. In some embodiments, the support pins may be configured to adjust the level of rolling resistance or interference fit.

Figure 18B:
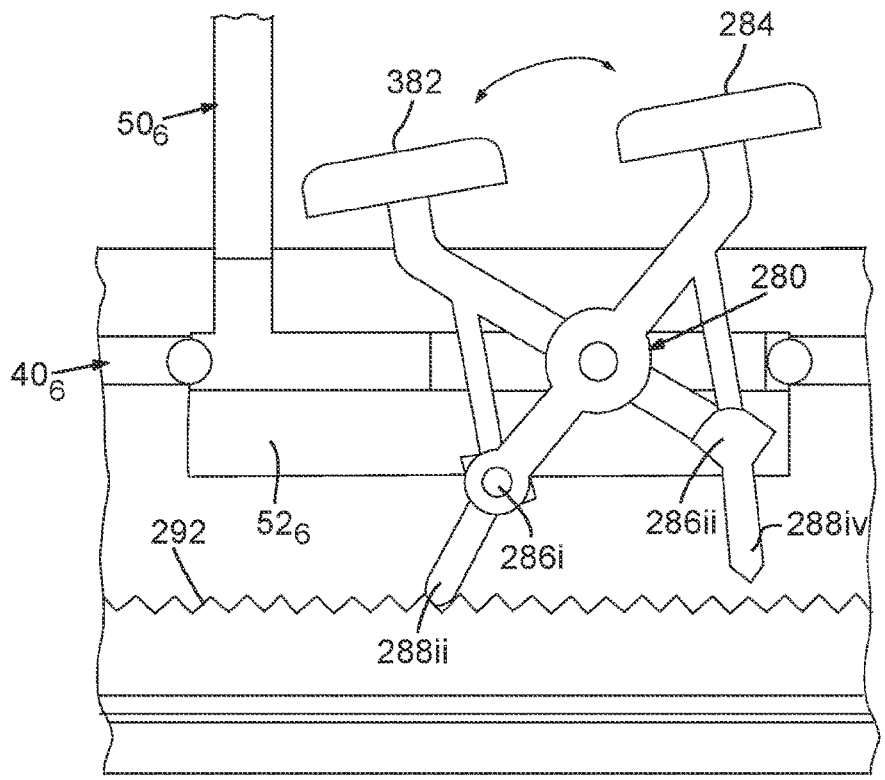
FIG. 18B is an enlarged fragmentary side elevation view of the guide structure of FIG. 18A showing a pinned lever-arm mechanical assembly used to selectively move and adjust the carriage.

FIG. 18B is an enlarged fragmentary side elevation view of guide structure 10 of FIG. 18A showing pinned lever-arm mechanical assembly 280 of undercarriage $52_6$ in an "unlocked" configuration. As shown in FIG. 18B, first lever arm 282 is pushed down relative to second lever arm 282 to free the third spring-lock leg (not shown) and fourth spring-lock leg $288_{iv}$ from, respectively, the first lever rack (not shown) and second lever rack 292, allowing carriage $50_6$ to move towards first and second closed ends (not shown) of base 12.

Example 7—Platform-Mounted Worm Drive Based Carriage Translation Actuator

Figure 19A:
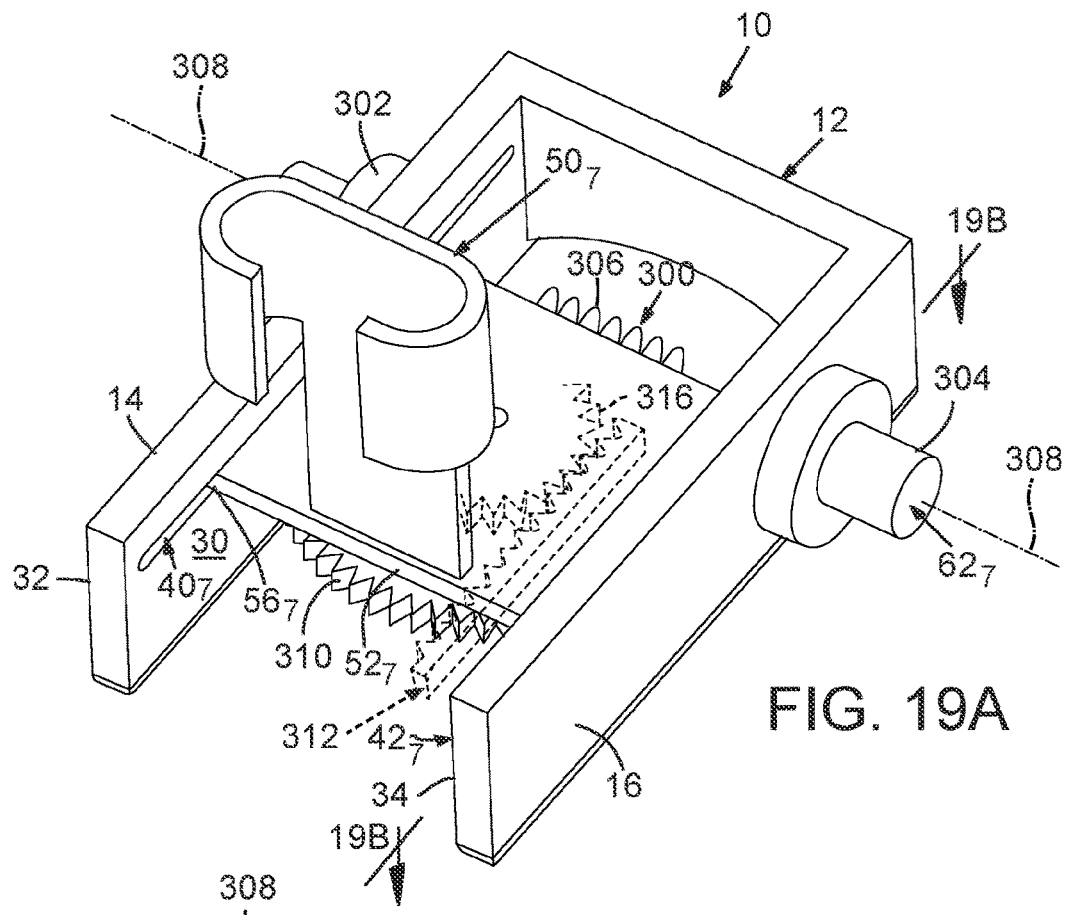
FIG. 19A is an isometric view of an alternative embodiment of the disclosed guide structure having a worm-gear based carriage translation actuator in operative association with the undercarriage to facilitate moving and adjusting the carriage of the guide structure along the first and second carriage guide surfaces of the base.

FIG. 19A is an isometric view of an alternative embodiment of guide structure 10, in which a worm-drive based carriage translation actuator $62_7$ is in operative association with an undercarriage $52_7$ having a worm drive assembly 300 to facilitate moving and adjusting a carriage $50_7$ along a first carriage guide surface $40_7$ and a second carriage guide surface $42_7$ of base 12. As shown in FIG. 19A, a rotational force may be applied to a first knob 302 and a second knob 304 to move a worm screw 306 about a worm-screw pivot axis 308 generally transverse to first arm 14 and second arm 16 and drive a worm wheel 310 set to mesh with a worm wheel rack 312 of undercarriage $52_7$ to move and adjust carriage $50_7$. In some embodiments, the diameter of first knob 302 or second knob 304 may be increased or decreased to provide for finer or coarser adjustments.

Figure 19B:
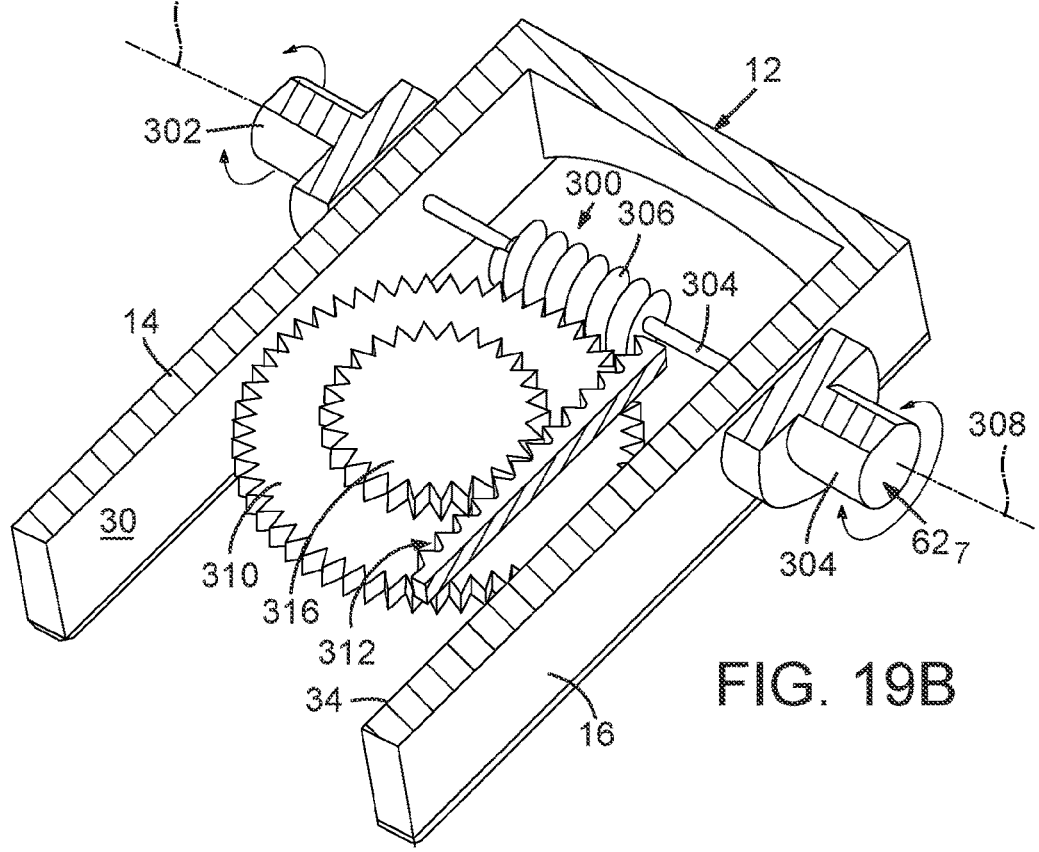
FIG. 19B is a sectional view taken along lines 19B-19B of FIG. 19A showing the worm-gear assembly of the carriage translation actuator of the guide structure mounted on a worm-gear platform extending between the arms of the base.

FIG. 19B is a sectional view taken along lines 19B-19B of the guide structure of FIG. 19A showing worm-drive assembly 300 of carriage translation actuator $62_7$ mounted on a worm-drive platform 314 formed from and extending between first interior surface 30 of first arm 14 and second interior surface 34 of second arm 16. As shown in FIG. 19B, a worm wheel gear 316 of worm wheel 310 is set to mesh with worm wheel rack 312 of undercarriage $52_7$ to move and adjust carriage $50_7$ along first and second carriage guide surfaces $40_7$ and $42_7$.

Example 8—Undercarriage-Mounted Worm Drive Based Carriage Translation Actuator

Figure 20A:
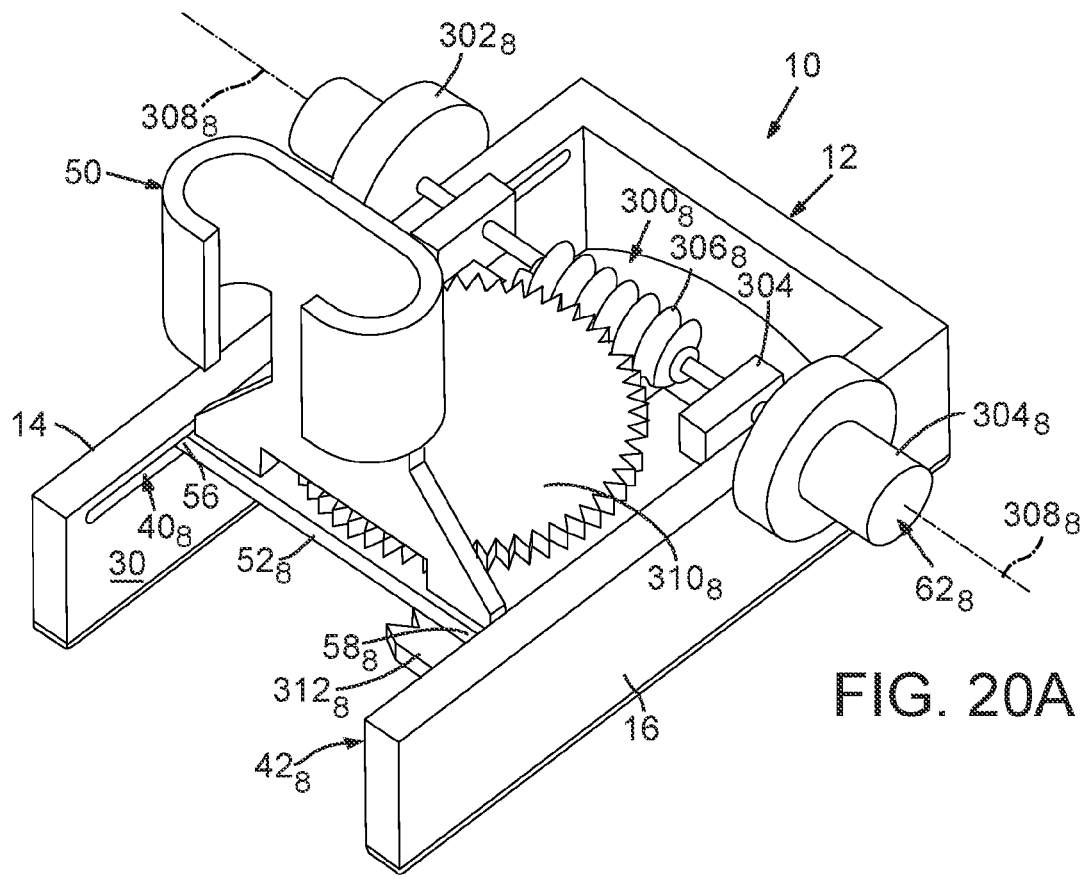
FIG. 20A is an isometric view of an alternative embodiment of the disclosed guide structure having a worm-gear based carriage translation actuator in operative association with the undercarriage to facilitate moving and adjusting the carriage of the guide structure along the guide surfaces of the base.

FIG. 20A is an isometric view of an alternative embodiment of guide structure 10, in which a worm-drive based carriage translation actuator $62_8$ is in operative association with an undercarriage $52_8$ having an undercarriage-mounted worm drive assembly $300_8$ to facilitate moving and adjusting a carriage $50_8$ along a first carriage guide surface $40_8$ and a second carriage guide surface $42_8$ of base 12. As shown in FIG. 20A, a rotational force may be applied to a first knob $302_8$ and a second knob $304_8$ to move a worm screw $306_8$ about a worm-screw pivot axis $308_8$ generally transverse to first arm 14 and second arm 16 and drive a worm wheel $310_8$ set to mesh with a worm wheel rack $312_8$ of undercarriage $52_8$ to move and adjust carriage $50_8$ relative to base 12. In some embodiments, the diameter of first knob $302_8$ or second knob $304_8$ may be increased or decreased to provide for finer or coarser adjustments.

Figure 20B:
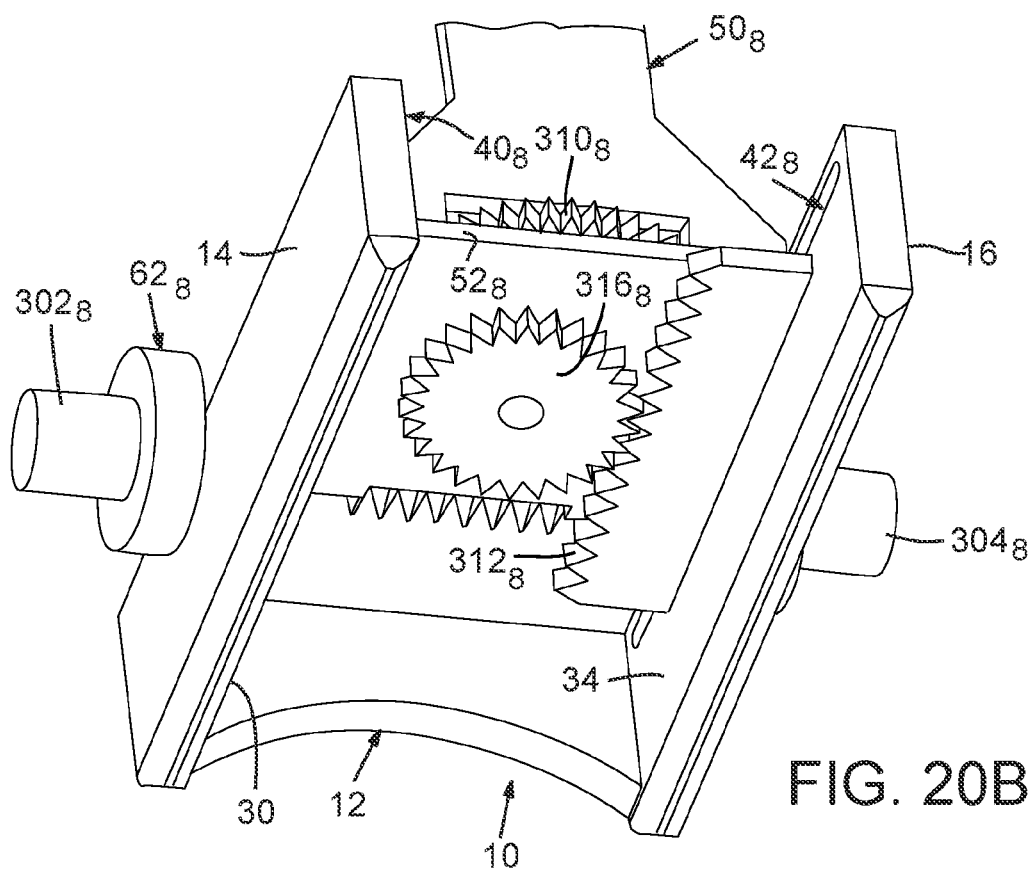
FIG. 20B is an oblique front-left bottom view showing the worm-gear assembly of the carriage translation actuator of the guide structure of 20A mounted on the undercarriage.

FIG. 20B is an oblique front-left bottom view showing worm wheel gear $316_8$ of worm wheel $310_8$ positioned beneath undercarriage $52_8$ and set to mesh with worm wheel rack $312_8$ to facilitate moving and adjusting carriage $50_8$ along first carriage guide surface $40_8$ and second carriage guide surface $42_8$. As shown in FIG. 20B, worm wheel rack $312_8$ is formed from second interior surface 34 of second arm 16. In some embodiments, worm wheel rack $312_8$ is formed from first interior surface 30 of first arm 14.

Example 9—Continuous-Spring Based Carriage Translation Actuator

Figure 21A:
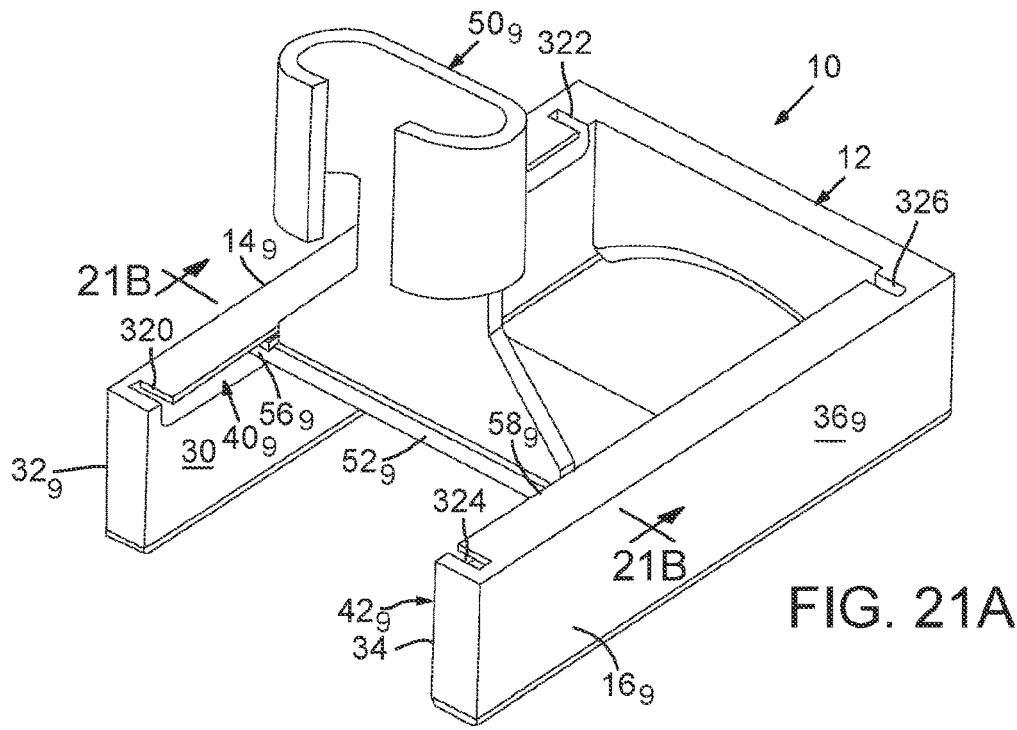
FIG. 21A is an isometric view of an alternative embodiment of the disclosed guide structure having a continuous-spring based carriage translation actuator in operative association with the undercarriage to facilitate moving and adjusting the carriage of the guide structure along the guide surfaces of the base.

FIG. 21A is an isometric view of an alternative embodiment of guide structure 10, in which a continuous-spring based carriage translation actuator $62_9$ is in operative association with an undercarriage $52_9$ having spring-loaded first and second support portions $56_9$ and $58_9$ set to create sliding resistance (i.e., an "interference fit") with first and second carriage guide surfaces $40_9$ and $42_9$ to secure a carriage $50_9$ to base 12. Carriage $50_9$ remains secured to base 12 until an external longitudinal force is applied to carriage $50_9$ to overcome the sliding resistance of spring-loaded first and second support portions $56_9$ and $58_9$ to facilitate moving and adjusting carriage $50_9$ along first and second carriage guide surfaces $40_9$ and $42_9$ of base 12. As shown in FIG. 21A, entry slots 320 and 322 are formed in a first external surface $32_9$ of first arm $14_9$ and entry slots 324 and 326 are formed in a second external surface $36_9$ to allow insertion or extraction of spring-loaded first and second support portions $56_9$ and $58_9$ into, respectively, first and second carriage guide surfaces $40_9$ and $42_9$. In some embodiments, first and second support portions $56_9$ and $58_9$ of undercarriage $52_9$ are compliant to base 12 and comprise a continuous spring mechanism to bias engaging first and second support portions $56_9$ and $58_9$ to base 12 and secure carriage $50_9$ in place. In some embodiments, first support portion $56_9$ and second support portion $58_9$ each comprise one or more support pins to constrain the movement of carriage $50_9$ along first and second carriage guide surfaces $40_9$ and $42_9$.

Figure 21B:
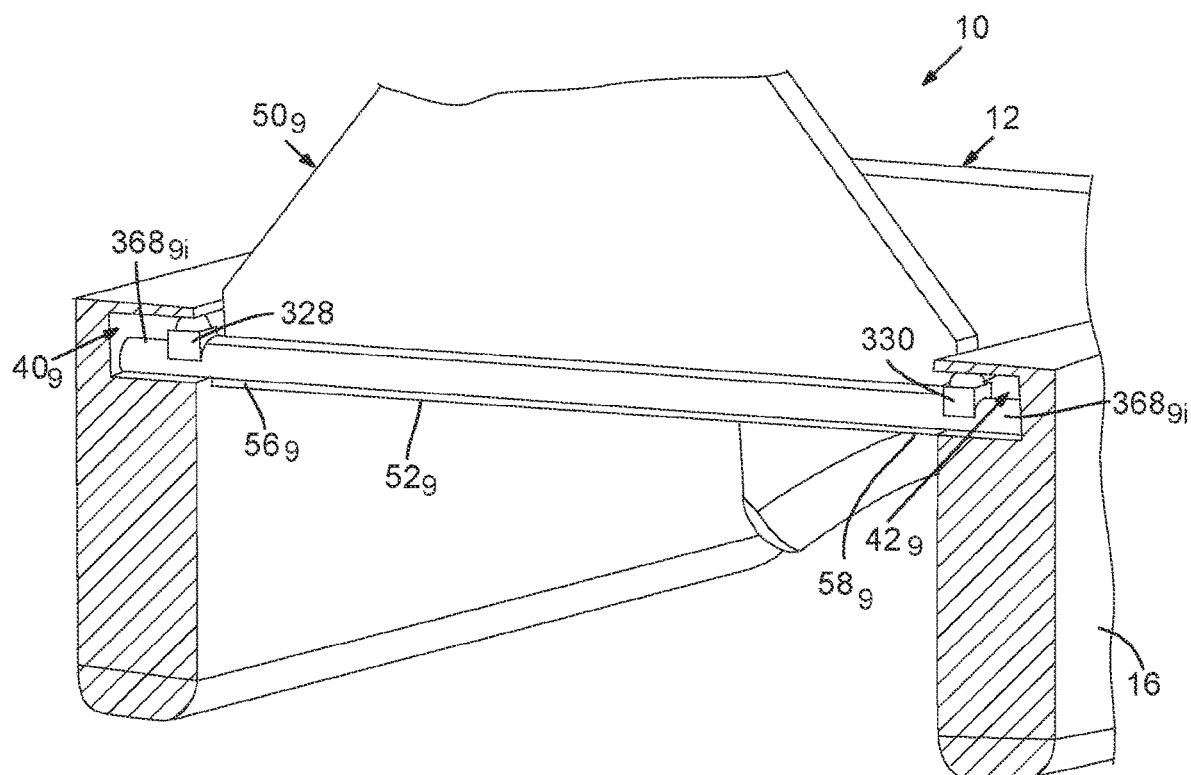
FIG. 21B is an enlarged fragmentary sectional view taken along lines 21B-21B of FIG. 21A showing support portions of the undercarriage of the guide structure having a continuous spring to create an interference fit with the guide surfaces to facilitate moving and adjusting the carriage of the guide structure.

FIG. 21B is a sectional view taken along lines 21B-21B of FIG. 21A, in which first and second support portions $56_9$ and $58_9$ of undercarriage $52_9$ of the guide structure of FIG. 21A comprise, respectively, a first continuous spring 328 and a second continuous spring 330 to create sliding resistance (i.e., an "interference fit") with, respectively, first and second carriage guide surfaces $40_9$ and $42_9$ to facilitate moving and adjusting the carriage of the guide structure. As shown in FIG. 21B, first and second continuous springs 328 and 330 are formed on and positioned above, respectively, a first support pin $268_{9i}$ of first support portion $56_9$ and a second support pin $268_{9ii}$ of second support portion $58_9$ to create the sliding resistance in the carriage guide surfaces and secure carriage $50_9$ to base 12 until an external longitudinal force is applied to carriage to overcome the sliding resistance of the continuous springs and thereby move and adjust the carriage.

Example 10—Elastomeric-Overmold Based Carriage Translation Actuator

Figure 22A:
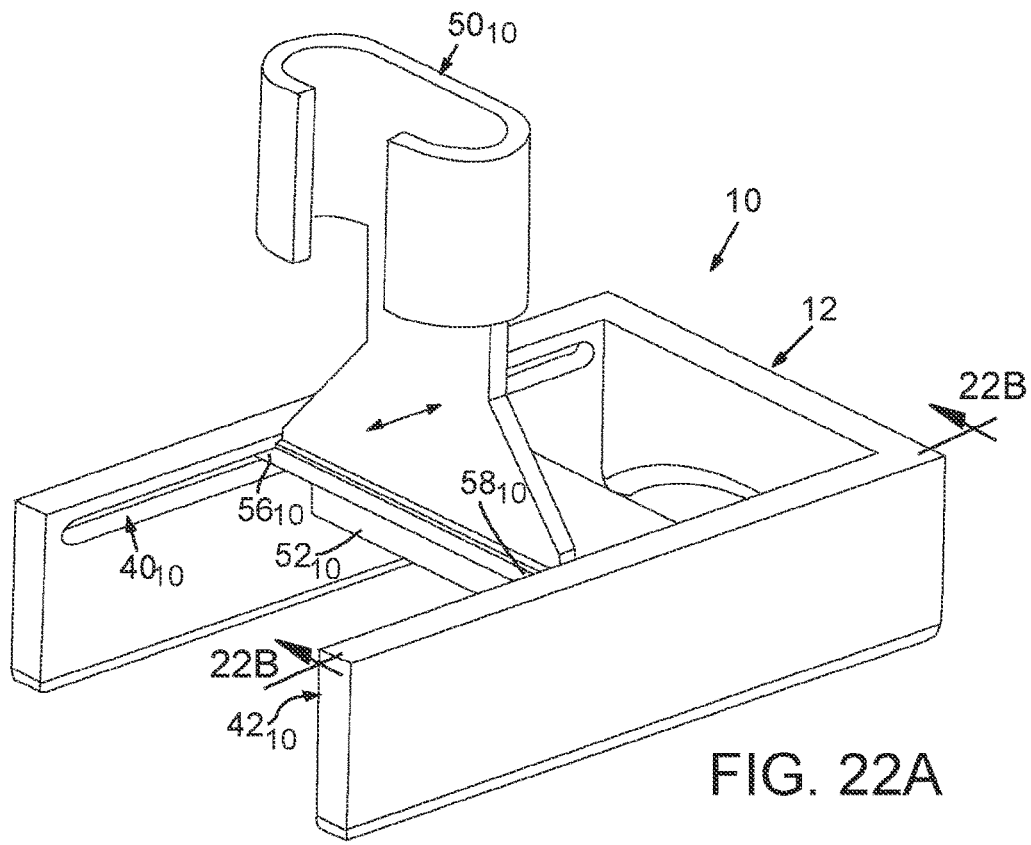
FIG. 22A is an isometric view of an alternative embodiment of the disclosed guide structure having an elastomeric-overmold based carriage translation actuator in operative association with the undercarriage to facilitate moving and adjusting the carriage of the guide structure along the guide surfaces of the base.

FIG. 22A is an isometric view of an alternative embodiment of guide structure 10, in which an elastomeric-overmold based carriage translation actuator $62_{10}$ is in operative association with an undercarriage $52_{10}$ to facilitate moving and adjusting a carriage $50_{10}$ along first and second carriage guide surfaces $40_{10}$ and $42_{10}$ of base 12. As shown in FIG. 22A, first and second carriage guide surfaces $40_{10}$ and $42_{10}$ comprise an elastomeric overmold material configured to create sliding resistance (i.e., an "interference fit") with, respectively, compliant first and second support portions $56_{10}$ and $58_{10}$ of undercarriage $52_{10}$ to engage them to base 12 and secure carriage $50_{10}$ in place.

Figure 22B:
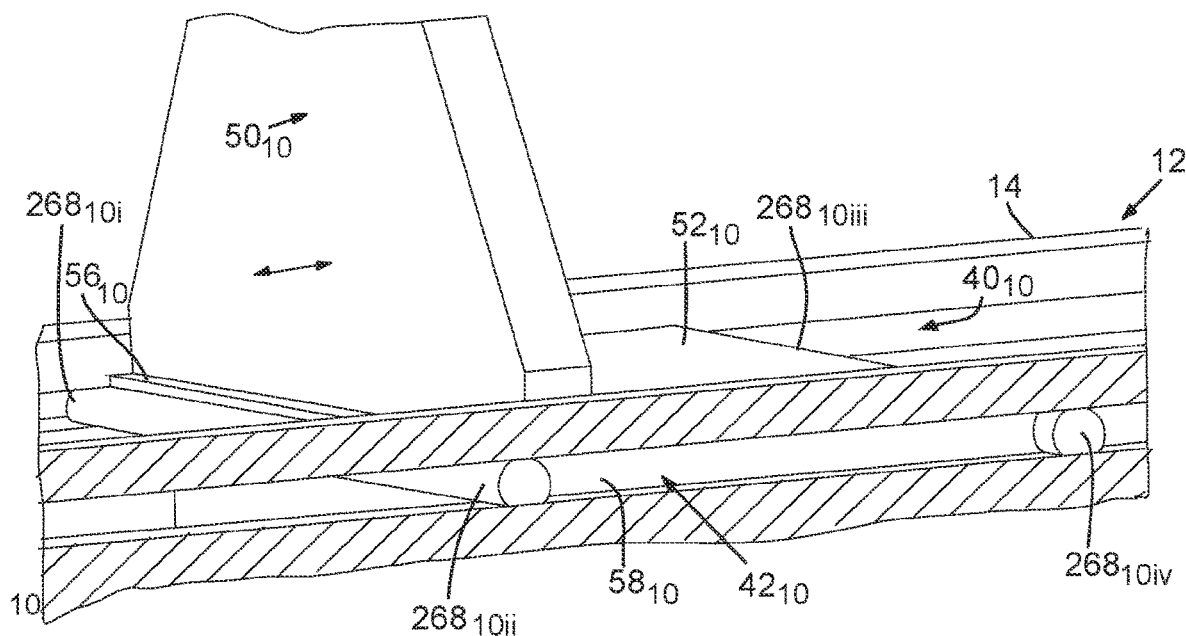
FIG. 22B is an enlarged fragmentary sectional view taken along lines 22B-22B of FIG. 21A showing guide surfaces of the guide structure, each having a compliant elastomeric overmold to create an interference fit with the support portions of the undercarriage to facilitate moving and adjusting the carriage of the guide structure.

FIG. 22B is a sectional view taken along lines 22B-22B of FIG. 22A, in which first and second carriage guide surfaces $40_{10}$ and $42_{10}$ of the guide structure of FIG. 22A each have an elastomeric overmold to create an interference fit with, respectively, compliant first and second support portions $56_{10}$ and $58_{10}$. As shown in FIG. 22B, first and third support pins $268_{10i}$ and $268_{10iii}$ of first support portion $56_{10}$ and second and fourth support pins $334_{10ii}$ and $338_{10iv}$ of second support portion $58_{10}$ are set in, respectively, overmolded first and second carriage guide surfaces $40_{10}$ and $42_{10}$ to create the sliding resistance in the carriage guide surfaces and secure carriage $50_9$ to base 12 until an external longitudinal force is applied to carriage to overcome the sliding resistance of the continuous springs and thereby move and adjust the carriage. In some embodiments, first support portion $56_{10}$ and second support portion $58_{10}$ of undercarriage $52_{10}$ each comprise one or more support pins to constrain the movement of carriage $50_{10}$ along first carriage guide surface $40_{10}$ and second carriage guide surface $42_{10}$.

Example 11—Bent Wire Support Assemblies

Figure 23A:
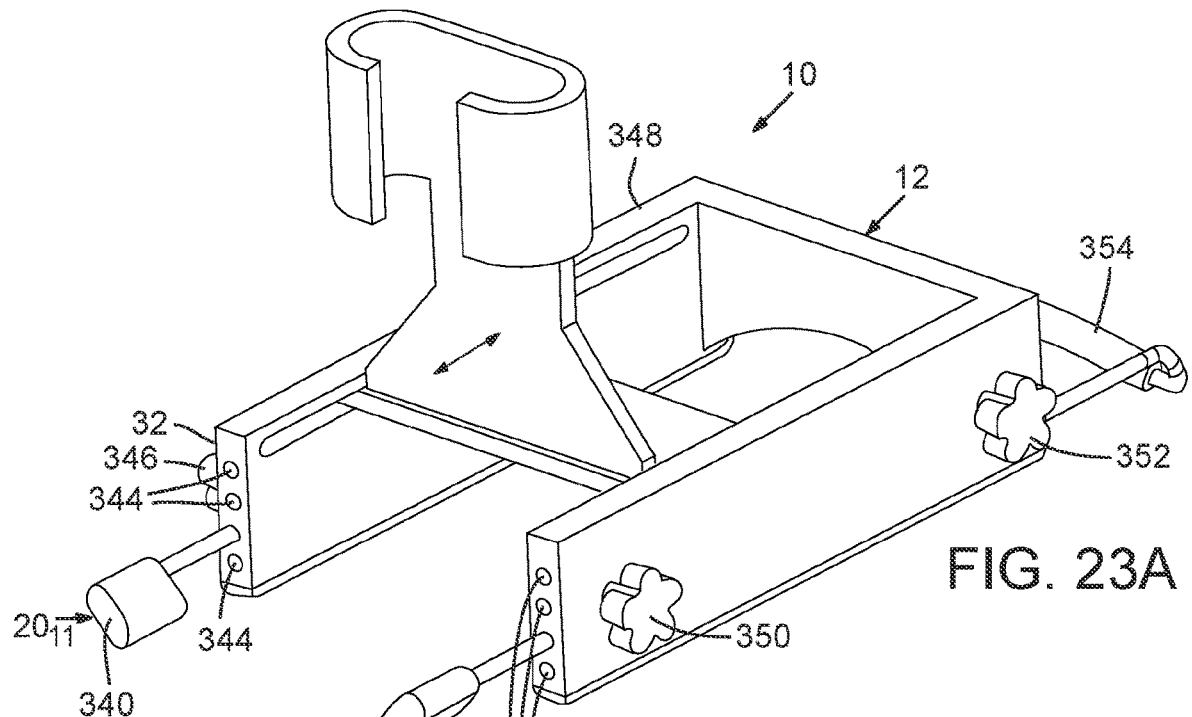
FIGS. 23A and 23B are, respectively, oblique front-right side and oblique rear-left side views of an alternative embodiment of the disclosed guide structure having bent-wire support assemblies that may be tailored to a specific patient or chosen site to provide additional stability to the guide structure when in use.
Figure 23B:
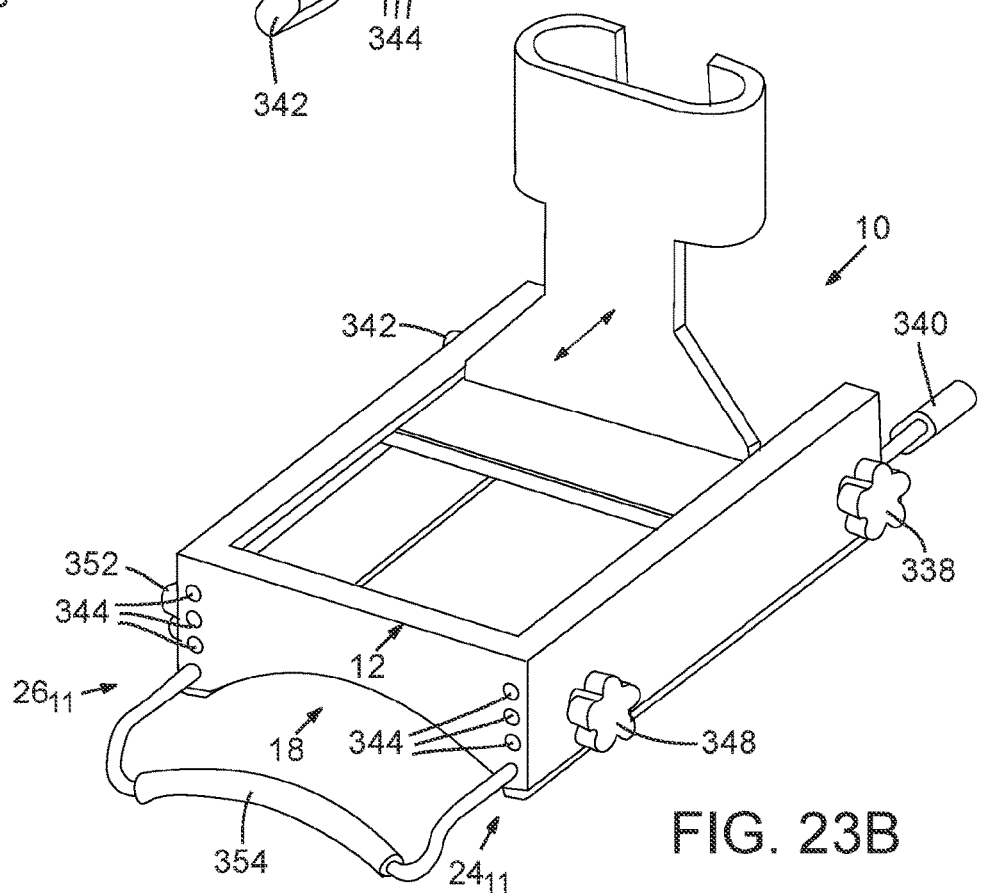

FIGS. 23A and 23B are, respectively, oblique front-right side and oblique rear-left side views of an alternative embodiment of guide structure 10, in which bent-wire support assemblies may be tailored to a specific patient or selected IV placement site to provide additional stability to the guide structure when in use. In some embodiments, first and second bent-wire bracing spurs 340 and 342 may be selectively mounted to base 12 by inserting the bent-wire bracing spurs into any one of a set of one or more mounting holes 344 to facilitate adjusting the distance between a medical probe (not shown) and the patient's skin during vascular line placement. As shown in FIG. 23A, a first mounting knob 346 secures bent-wire bracing spur 340 in a mounting hole 344 positioned at a first open end $20_{11}$ and a second mounting knob 348 secures bent-wire bracing spur 340 in a mounting hole 344 positioned at second open end $22_{11}$ to facilitate securing guide structure 10 to a patient's limb, neck, or torso. As shown in FIG. 23A, a third mounting knob 350 and a fourth mounting knob 352 secure a bent-wire limb restraint 354 to base 12.

FIG. 23B shows third and fourth mounting knobs 350 and 352 securing bent-wire limb restraint 354 in a mounting hole 344 positioned at a second close end $26_{11}$ and a mounting hole 344 positioned at first closed end $24_{11}$ for impeding a patient's limb, neck, or torso from entering open space 18. Skilled persons will understand that bent-wire limb restraint 354 may also be configured to function as a neck restraint or a torso restraint by adjusting the size of bent-wire limb restraint 354 to encircle a patient's neck or torso. In some embodiments, the length of the bent wire may be adjusted to create more or less "overhang" of the bent-wire assemblies relative to base 12. In some embodiments, the gauge of the bent wire may be tuned to provide compliance as needed. In some embodiments, an overmold or a coating may be applied to the bent wire to facilitate a patient's comfort and enhance the stability of guide structure 10 when secured to a patient's limb, neck, or torso.

It will be obvious to those having skill in the art that many changes may be made to the details of the above-described embodiments without departing from the underlying principles of the invention. The scope of the present invention should, therefore, be determined only by the following claims.

The invention claimed is:

1. A guide structure configured for placement on a patient's skin and to hold a medical probe and adjustably position the medical probe over a region of a surface of the patient's skin, comprising:
   a base configured to rest on the surface of the patient's skin, the base including first and second arms separated by an open space and having respective first and second open ends and respective first and second closed ends interconnected by a medial section, the first arm having a first interior surface and a first exterior surface, and the second arm having a second interior surface and a second exterior surface, the first and second interior surfaces being opposed to each other;
   a first carriage guide surface extending lengthwise between the first open and closed ends of the first arm;
   a second carriage guide surface extending lengthwise between the second open and closed ends of the second arm, the first and second carriage guide surfaces being plane parallel to each other;
   a first carriage adjustment channel formed lengthwise between the first open and closed ends of the first arm and including a lengthwise extending first gear rack;
   a second carriage adjustment channel formed lengthwise between the second open and closed ends of the second arm and including a lengthwise extending second gear rack, the first and second carriage adjustment channels being spatially aligned with each other and in spaced-apart relation to the first and second carriage guide surfaces;
   a carriage including an undercarriage and a carriage post, the undercarriage including first and second support portions laterally extending in opposite directions relative to one another, the first and second support portions configured to move along the respective first and second carriage guide surfaces and thereby form a movable bridge spanning the open space separating the first and second arms of the base, the carriage further including first and second spaced-apart shaft tunnels extending in a direction transverse to the first and second arms of the base;

a medical probe holder operatively connected to the carriage post and configured for motion transverse to the first and second arms to set, to a desired distance into the open space separating the first and second arms, a medical probe placed in the medical probe holder; and a carriage translation actuator in operative association with the undercarriage to move the carriage and thereby adjust a position of the medical probe over the surface of the patient's skin on which the base has been set, wherein the carriage translation actuator further comprises:

an actuator shaft sized to fit into one of the first and second shaft tunnels of the carriage and having opposite ends on which first and second drive gears are set to mesh with the respective first and second gear racks; and a follower shaft sized to fit into the other one of the first and second shaft tunnels of the carriage and having opposite ends on which first and second follower gears are set to mesh with the respective first and second gear racks, whereby the operative association of the carriage translation actuator and the undercarriage includes, in response to a rotational force applied to the actuator shaft, rotation of the actuator shaft and thereby rotation of the follower shaft and movement of the carriage to adjust the position of the medical probe over the surface of the patient's skin on which the base has been set.

2. The guide structure of claim 1, in which the carriage constitutes a carriage assembly of separate components that are fastened together and includes first, second, third, and fourth spaced-apart tunnel bisections, the third and fourth tunnel bisections being spatially aligned with, and having complementary shape to, the respective first and second tunnel bisections to form the first and second spaced-apart shaft tunnels through which the actuator shaft and the follower shaft pass.

3. The guide structure of claim 1, in which the base is divided into an enclosure component and a gearing component along a plane extending through the first and second carriage adjustment channels, the enclosure and gearing components having, respectively, mutually facing enclosure and gearing aspects extending along the plane, and further comprising:

a set of spaced-apart enclosure pins formed on the enclosure aspect of the enclosure component; and a set of base blind holes formed along the gearing aspect of the gearing component, each one of the base blind holes in the set configured and positioned to receive a corresponding one of the enclosure pins from the enclosure component and thereby combine the enclosure and gearing components to form the base.

4. The guide structure of claim 1, in which the first and second carriage adjustment channels each measure within a range of 1.0 centimeters to 13.0 centimeters lengthwise between, respectively, the first open and closed ends of the first arm and second open and closed ends of the second arm for variable placement of the medical probe relative to the surface of the patient's skin.

5. The guide structure of claim 1, in which the carriage of the guide structure is configured within a range of 0.1 centimeter to 8.0 centimeters of motion transverse to the first and second arms of the base for variable placement of the medical probe relative to the surface of the patient's skin.

6. The guide structure of claim 1, in which the medical probe holder is configured within a range of 0.1 centimeter to 8.0 centimeters of motion transverse to the first and second arms to set, to the desired distance into the open space separating the first and second arms, the medical probe placed in the medical device holder.

7. The guide structure of claim 1, in which the medial section of the base of the guide structure has a third exterior surface, and in which the first, second, and third exterior surfaces of the base have skin-facing friction portions for securing the guide structure to the surface of the patient's skin.

8. The guide structure of claim 1, in which the carriage post of the carriage has a carriage post through-hole configured to receive a carriage post fastener, and in which the medical probe holder further comprises a set of mutually spaced-apart hollows, the set of mutually spaced-apart hollows being positioned to selectively receive the carriage post fastener through the carriage post through-hole to set, to a desired distance into the open space separating the first and second arms, the medical probe placed in the medical device holder.

9. The guide structure of claim 1, in which the first and second carriage guide surfaces constitute, respectively, first and second support slots, and the first and second support portions of the undercarriage being sized to fit into and move along the respective first and second support slots to direct a motion of the undercarriage.

10. The guide structure of claim 1, further comprising first and second restraint anchors positioned on, respectively, the first and second exterior surfaces of the base of the guide structure for supporting a limb restraint, a neck restraint, or a torso restraint.

11. The guide structure of claim 10, in which the first and second restraint anchors are positioned proximal to, respectively, the first and second closed ends of the base of the guide structure relative to the first and second open ends of the base of the guide structure.

12. The guide structure of claim 1, in which the medical probe holder includes a rail bracket that extends along the length of the medical probe holder and the carriage post includes a guide rail having a complementary shape to that of the rail bracket, the guide rail and the rail bracket forming a friction fit to set in non-discrete increments, to a desired distance into the open space separating the first and second arms, the medical probe placed in the medical probe holder.

13. The guide structure of claim 1, in which the carriage post includes a mounting arm that, at a distal end relative to the carriage post, is pivotally connected to the medical probe holder for movement about a first pivot axis generally transverse to the first and second arms.

14. The guide structure of claim 1, in which the carriage post and the medical probe holder are linked by an elastomeric spring for providing naturally restorative force to the medical probe placed in the medical probe holder.

15. The guide structure of claim 1, in which the guide structure is made of medical grade materials to allow for sterilization of the guide structure prior to use.

16. The guide structure of claim 1, in which the guide structure is made of polylactic acid to allow the guide structure to be biodegradable.

17. A guide structure configured for placement on a patient's skin and to hold a medical probe and adjustably position the medical probe over a region of a surface of the patient's skin, comprising:

a base configured to rest on the surface of the patient's skin, the base including first and second arms separated by an open space and having respective first and second open ends and respective first and second closed ends interconnected by a medial section, the first arm having a first interior surface and a first exterior surface, and the second arm having a second interior surface and a second exterior surface, the first and second interior surfaces being opposed to each other;

first and second bracing spurs positioned on, respectively, the first and second arms of the base of the guide structure for impeding the patient's limb, neck, or torso from entering the open space of the base;

a first carriage guide surface extending lengthwise between the first open and closed ends of the first arm;

a second carriage guide surface extending lengthwise between the second open and closed ends of the second arm, the first and second carriage guide surfaces being plane parallel to each other;

a carriage including an undercarriage and a carriage post, the undercarriage including first and second support portions laterally extending in opposite directions relative to one another, the first and second support portions configured to move along the respective first and second carriage guide surfaces and thereby form a movable bridge spanning the open space separating the first and second arms of the base;

a medical probe holder operatively connected to the carriage post and configured for motion transverse to the first and second arms to set, to a desired distance into the open space separating the first and second arms, a medical probe placed in the medical probe holder; and a carriage translation actuator in operative association with the undercarriage to move the carriage and thereby adjust a position of the medical probe over the surface of the patient's skin on which the base has been set.

18. The guide structure of claim 17, in which the first and second bracing spurs are positioned at, respectively, the first and second open ends of the first and second arms of the base.

19. The guide structure of claim 17, in which the first and second bracing spurs are positioned on, respectively, the first and second interior surfaces of the first and second arms of the base and extend into the open space.

20. The guide structure of claim 17, in which the first and second bracing spurs have curved skin-facing aspects for contouring the first and second bracing spurs to a surface of the patient's limb, neck, or torso.

21. A guide structure configured for placement on a patient's skin and to hold a medical probe and adjustably position the medical probe over a region of a surface of the patient's skin, comprising:

a base configured to rest on the surface of the patient's skin, the base including first and second arms separated by an open space and having respective first and second open ends and respective first and second closed ends interconnected by a medial section, the first arm having a first interior surface and a first exterior surface, and the second arm having a second interior surface and a second exterior surface, the first and second interior surfaces being opposed to each other;

a first carriage guide surface extending lengthwise between the first open and closed ends of the first arm;

a second carriage guide surface extending lengthwise between the second open and closed ends of the second arm, the first and second carriage guide surfaces being plane parallel to each other;

a carriage including an undercarriage and a carriage post, the undercarriage including first and second support portions laterally extending in opposite directions relative to one another, the first and second support portions configured to move along the respective first and second carriage guide surfaces and thereby form a movable bridge spanning the open space separating the first and second arms of the base;

a medical probe holder operatively connected to the carriage post and configured for motion transverse to the first and second arms to set, to a desired distance into the open space separating the first and second arms, a medical probe placed in the medical probe holder;

a carriage translation actuator in operative association with the undercarriage to move the carriage and thereby adjust a position of the medical probe over the surface of the patient's skin on which the base has been set;

a reel-based restraint system including an extended base, a tightening spool, and a release spool, the extended base positioned on the medial section and having first and second limb restraints;

a cable guided by the tightening spool and rotationally linked to the release spool, the tightening spool positioned on either the first or the second limb restraint, the tightening spool including a manual control for manually winding a length of the cable around the release spool to tighten the first and second limb restraints around the patient's limb; and a release actuator operatively connected to the release spool for selectively unwinding a length of the cable around the release spool to loosen the first and second limb restraints around the patient's limb.

* * * * *